US010391019B2

(12) United States Patent
Stryker et al.

(10) Patent No.: US 10,391,019 B2
(45) Date of Patent: Aug. 27, 2019

(54) PATIENT SUPPORT WITH UNIVERSAL ENERGY SUPPLY SYSTEM

(71) Applicant: Stryker Corporation, Kalamazoo, MI (US)

(72) Inventors: Martin W. Stryker, Kalamazoo, MI (US); Krishna Sandeep Bhimavarapu, Kalamazoo, MI (US); Richard A. Derenne, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/477,326

(22) Filed: Apr. 3, 2017

(65) Prior Publication Data

US 2017/0202728 A1 Jul. 20, 2017

Related U.S. Application Data

(63) Continuation of application No. 14/549,226, filed on Nov. 20, 2014, now Pat. No. 9,642,759, which is a (Continued)

(51) Int. Cl.
*A61G 7/00* (2006.01)
*A61H 9/00* (2006.01)
(Continued)

(52) U.S. Cl.
CPC ............ *A61H 9/0078* (2013.01); *A61G 7/001* (2013.01); *A61G 7/0005* (2013.01); *A61G 7/012* (2013.01); *A61G 7/015* (2013.01); *A61G 7/018* (2013.01); *A61G 7/05* (2013.01); *A61G 7/0506* (2013.01); *A61G 7/1015* (2013.01); *A61G 7/1019* (2013.01); *A61G 7/1026* (2013.01); *A61G 7/1055* (2013.01); *A61G 10/005* (2013.01); *A61G 13/107* (2013.01); *A61M 13/003* (2013.01); *A61M 16/1005* (2014.02); *A61H 2201/1238* (2013.01); *A61H 2205/10* (2013.01); (Continued)

(58) Field of Classification Search
CPC ........................................................ A61G 7/00
USPC .................... 5/600, 613, 615, 713, 421, 423
See application file for complete search history.

(56) References Cited

U.S. PATENT DOCUMENTS 4,584,989 A 4/1986 Stith
4,768,241 A 9/1988 Beney
(Continued)

FOREIGN PATENT DOCUMENTS

GB 2214678 A 9/1989

OTHER PUBLICATIONS

PCT Search Report dated Aug. 7, 2008 for corresponding PCT International Application No. PCT/US08/59006.

*Primary Examiner* — Frederick C Conley
(74) *Attorney, Agent, or Firm* — Warner Norcross + Judd LLP

(57) ABSTRACT

A patient support includes a patient support surface, a DVT pump mounted in the patient support, and a port mounted at the patient support in selective fluid communication with the DVT pump. Optionally, the patient support further includes a control system to detect when a DVT device is coupled or in close proximity to the port and/or the type of DVT device. Further, the control system may be configured to control the pump based on the type of DVT device coupled to the port.

20 Claims, 30 Drawing Sheets

Related U.S. Application Data continuation-in-part of application No. 13/220,106, filed on Aug. 29, 2011, now Pat. No. 8,914,924, which is a continuation-in-part of application No. 12/057,941, filed on Mar. 28, 2008, now Pat. No. 8,011,039.

(60) Provisional application No. 60/923,501, filed on Apr. 13, 2007, provisional application No. 60/968,780, filed on Aug. 29, 2007.

(51) Int. Cl.
| | | |
|---|---|---|
| A61G 7/05 | (2006.01) | |
| A61G 7/018 | (2006.01) | |
| A61G 7/012 | (2006.01) | |
| A61G 7/10 | (2006.01) | |
| A61G 10/00 | (2006.01) | |
| A61G 13/10 | (2006.01) | |
| A61M 13/00 | (2006.01) | |
| A61M 16/10 | (2006.01) | |
| A61G 7/015 | (2006.01) | |

(52) U.S. Cl.
CPC ............ *A61M 2202/0208* (2013.01); *A61M 2210/0606* (2013.01); *A61M 2210/086* (2013.01)

(56) References Cited

U.S. PATENT DOCUMENTS

| | | |
|---|---|---|
| 4,797,962 A | 1/1989 | Goode |
| 5,236,004 A | 8/1993 | Sunderland et al. |
| 5,251,347 A | 10/1993 | Hopper et al. |
| 5,630,238 A | 5/1997 | Weismiller et al. |
| 5,713,856 A | 2/1998 | Eggers et al. |
| 5,749,374 A | 5/1998 | Schneider, Sr. |
| 5,843,007 A | 12/1998 | McEwen et al. |
| 5,951,502 A | 9/1999 | Peeler et al. |
| 5,991,947 A | 11/1999 | Lavin et al. |
| 6,062,244 A | 5/2000 | Arkans |
| 6,155,260 A | 12/2000 | Lavin et al. |
| 6,231,532 B1 | 5/2001 | Watson et al. |
| 6,387,065 B1 * | 5/2002 | Tumey ................. A61H 9/0078 601/152 |
| 6,440,093 B1 * | 8/2002 | McEwen ............. A61H 9/0078 601/148 |
| 6,544,202 B2 | 4/2003 | McEwen et al. |
| 6,546,577 B1 | 4/2003 | Chinn |
| 6,553,588 B2 | 4/2003 | Hensley et al. |
| 6,735,799 B1 | 5/2004 | Ellis et al. |
| 6,736,787 B1 | 5/2004 | McEwen et al. |
| 6,829,796 B2 | 12/2004 | Salvatini et al. |
| 6,884,255 B1 | 4/2005 | Newton |
| 6,895,715 B2 | 5/2005 | Gallant et al. |
| 6,988,423 B2 | 1/2006 | Bolam et al. |
| 7,017,208 B2 | 3/2006 | Weismiller et al. |
| 7,076,993 B2 | 7/2006 | Cook |
| 7,256,771 B2 | 8/2007 | Novak et al. |
| 7,354,410 B2 | 4/2008 | Perry et al. |
| 7,354,411 B2 | 4/2008 | Perry et al. |
| 7,398,803 B2 | 7/2008 | Newton |
| 7,490,620 B2 | 2/2009 | Tesluk et al. |
| 7,591,796 B1 | 9/2009 | Barak et al. |
| 7,641,623 B2 | 1/2010 | Biondo et al. |
| 7,644,458 B2 | 1/2010 | Foster et al. |
| 7,669,263 B2 | 3/2010 | Menkedick et al. |
| 7,741,966 B2 | 6/2010 | Bonnefin et al. |
| 7,753,977 B2 | 7/2010 | Lyons et al. |
| 7,810,519 B2 | 10/2010 | Tesluk et al. |
| 7,904,976 B2 | 3/2011 | Hakamiun et al. |
| 7,909,786 B2 | 3/2011 | Bonnefin et al. |
| 8,011,039 B2 | 9/2011 | Stryker et al. |
| 8,235,922 B2 | 8/2012 | Rowe et al. |
| 8,256,459 B2 | 9/2012 | Tesluk et al. |
| 8,257,286 B2 | 9/2012 | Meyer et al. |
| 8,257,287 B2 | 9/2012 | Hanlon et al. |
| 8,287,517 B2 | 10/2012 | Hanlon et al. |
| 8,506,507 B2 | 8/2013 | Bock |
| 8,585,622 B2 | 11/2013 | Mros et al. |
| 8,734,369 B2 | 5/2014 | Perry et al. |
| 8,845,562 B2 | 9/2014 | Receveur et al. |
| 2003/0195644 A1 * | 10/2003 | Borders ............... A47C 31/008 700/90 |
| 2006/0258964 A1 * | 11/2006 | Biondo ................ A61H 9/0078 601/152 |
| 2010/0076356 A1 | 3/2010 | Biondo et al. |
| 2013/0014324 A1 | 1/2013 | Receveur et al. |
| 2013/0231596 A1 | 9/2013 | Hornbach et al. |
| 2013/0282047 A1 | 10/2013 | Hanlon et al. |
| 2013/0331748 A1 | 12/2013 | Wright et al. |
| 2014/0031730 A1 | 1/2014 | Hornbach et al. |
| 2014/0058301 A1 | 2/2014 | Mros et al. |
| 2014/0094726 A1 | 4/2014 | Malhi et al. |
| 2014/0207036 A1 | 7/2014 | Perry et al. |
| 2014/0249458 A1 | 9/2014 | Malhi et al. |
| 2015/0094623 A1 | 4/2015 | Howell et al. |

* cited by examiner

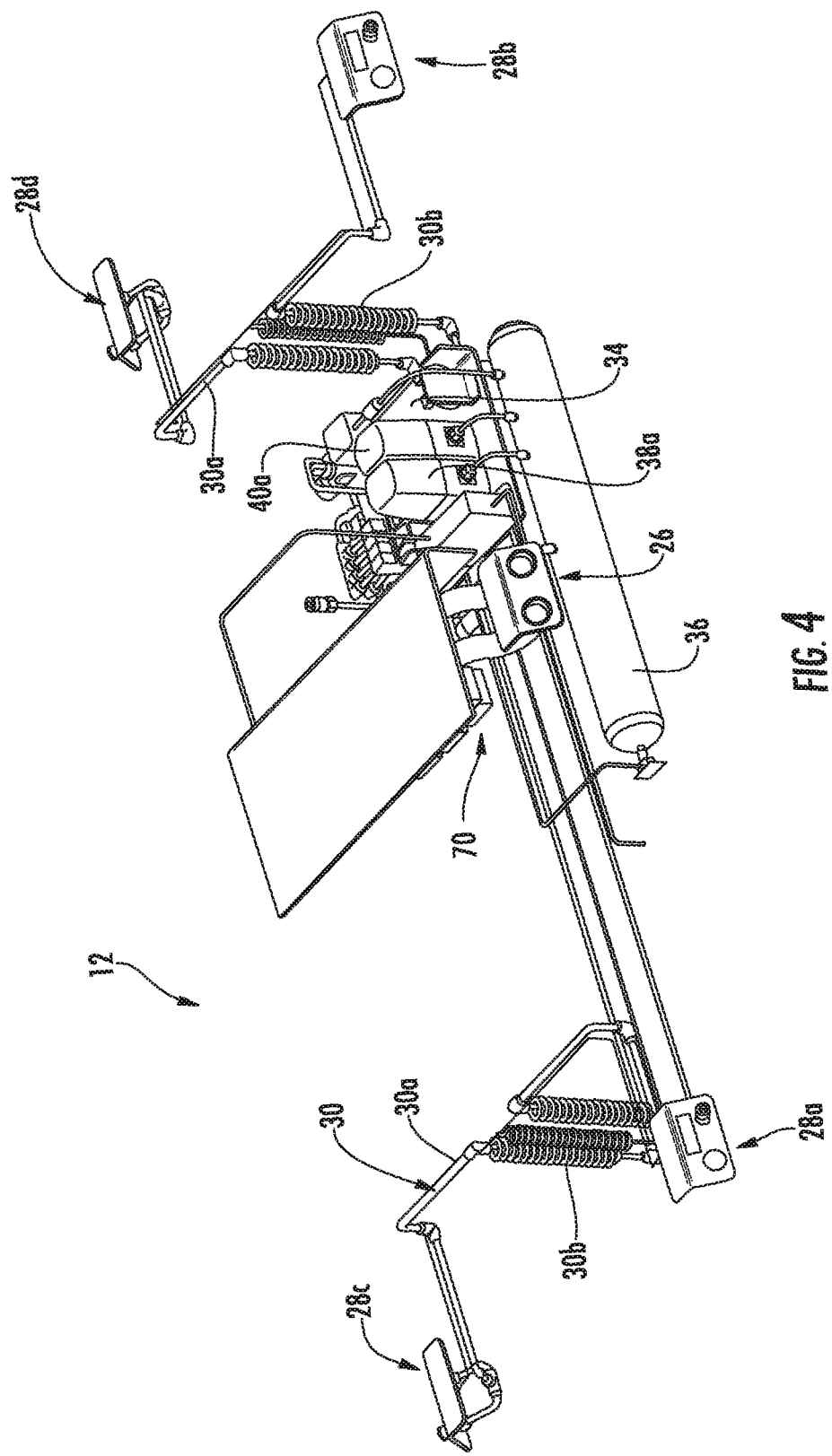

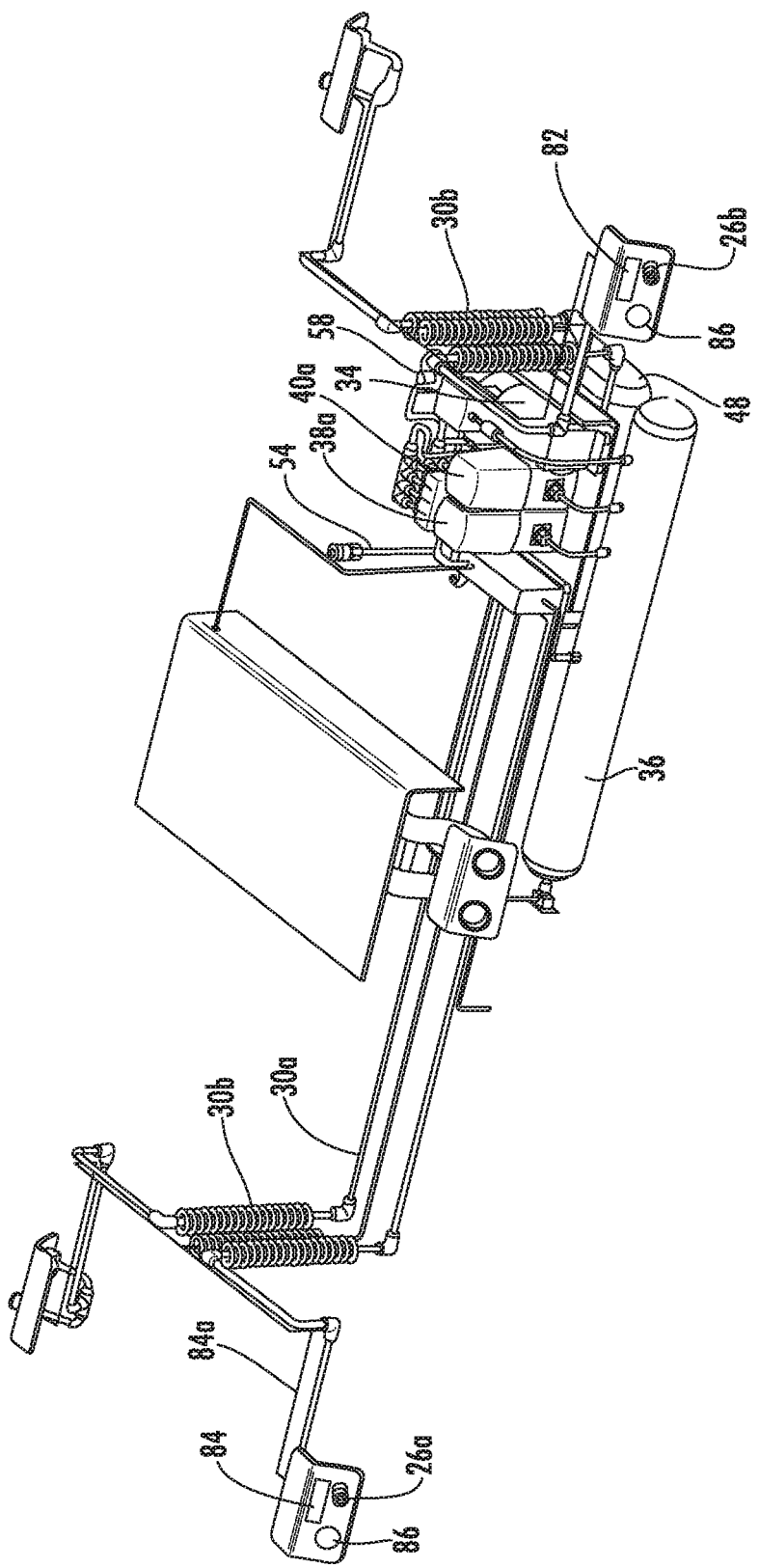

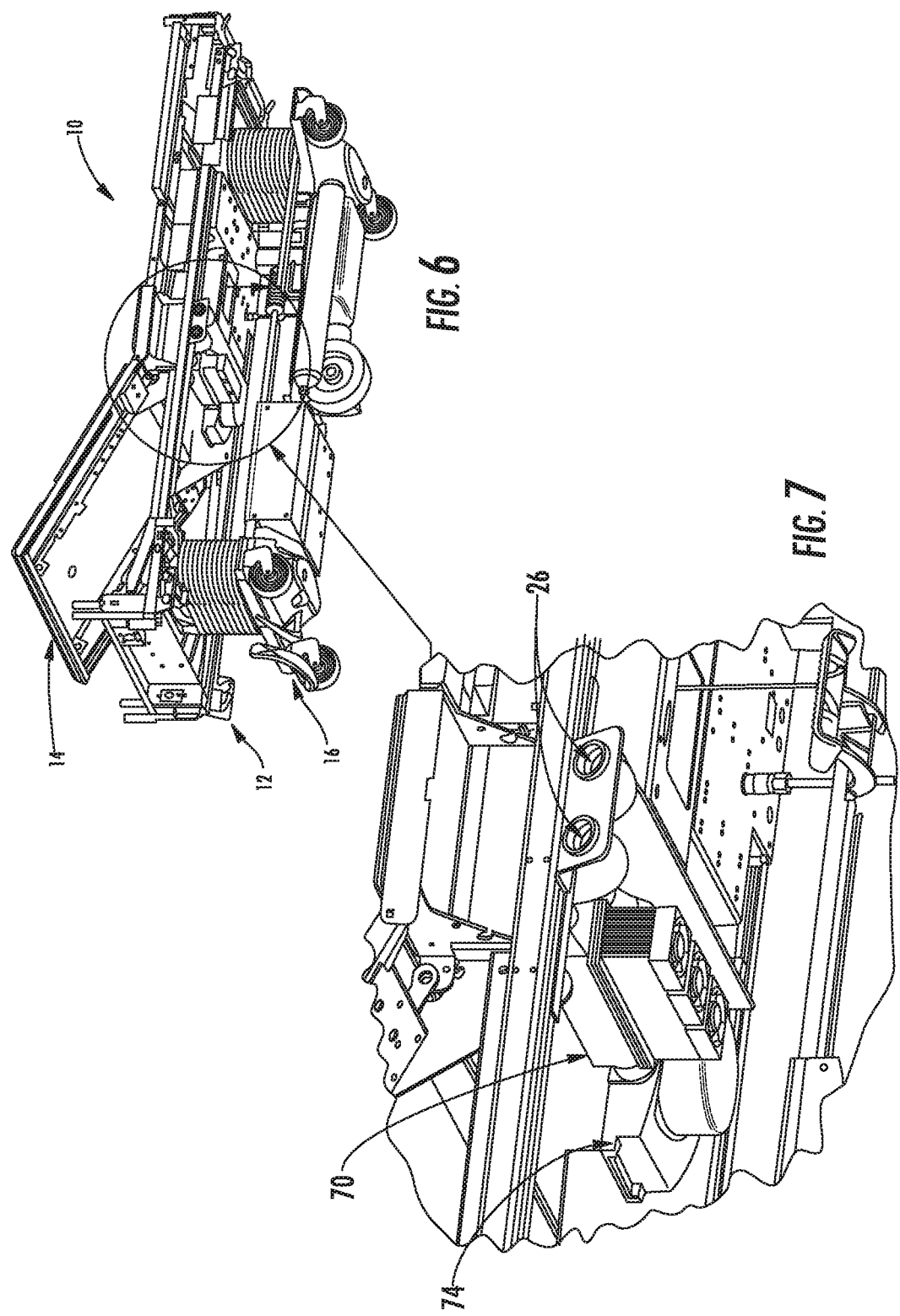

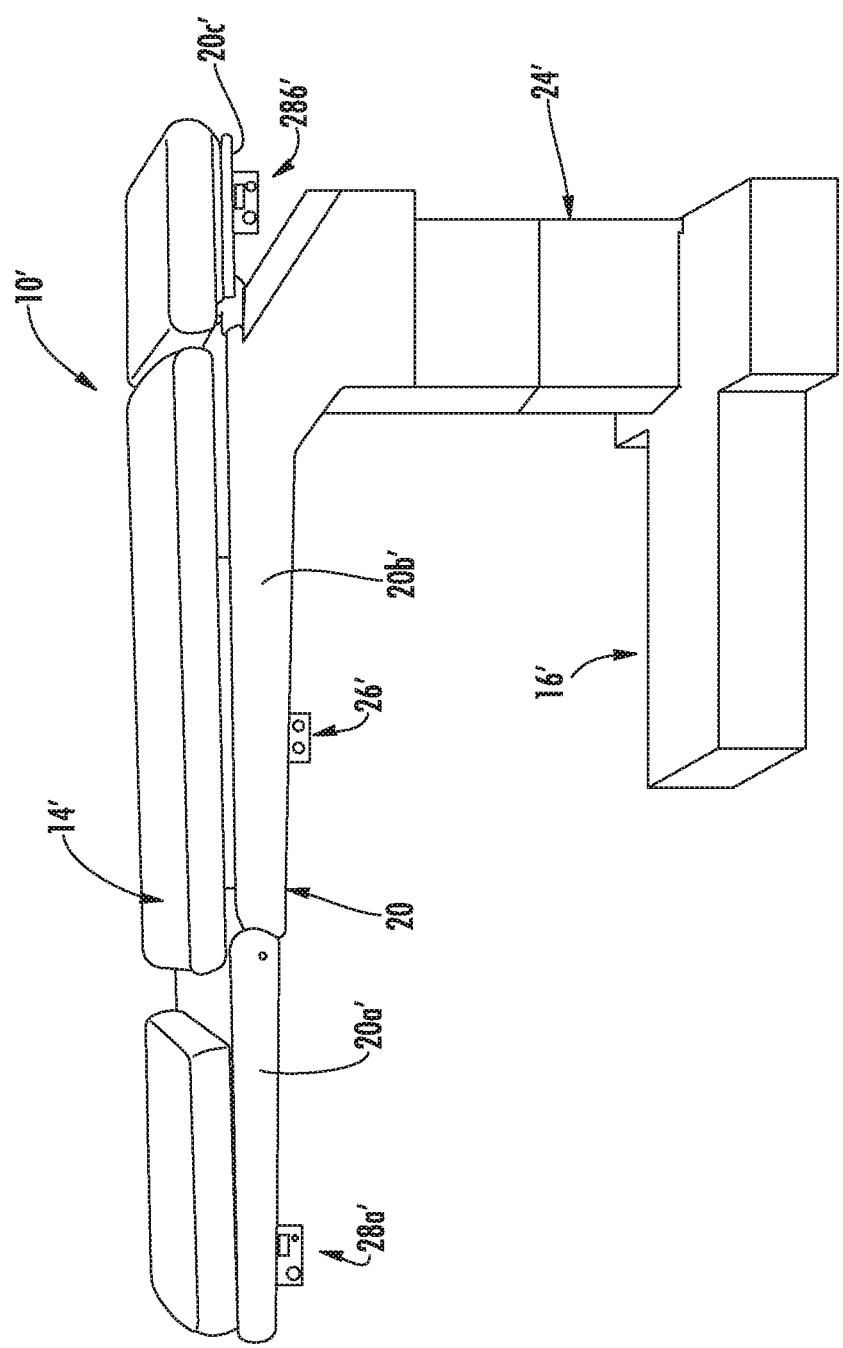

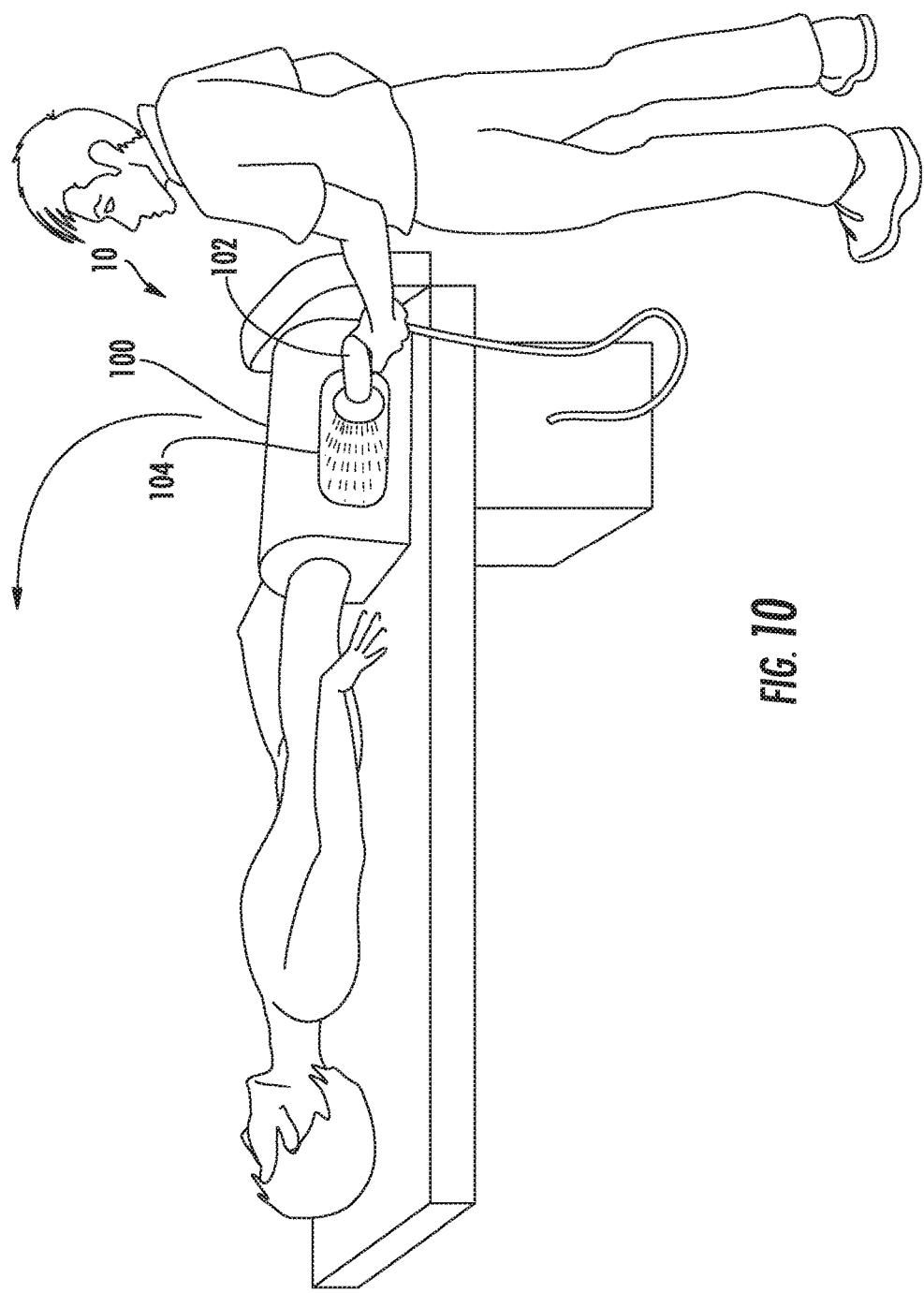

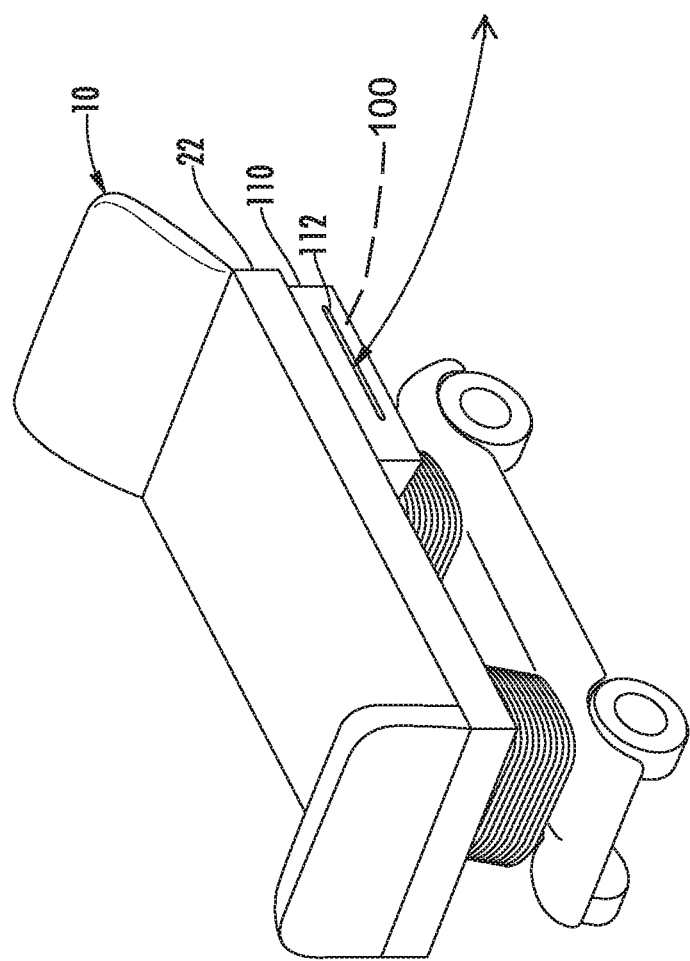

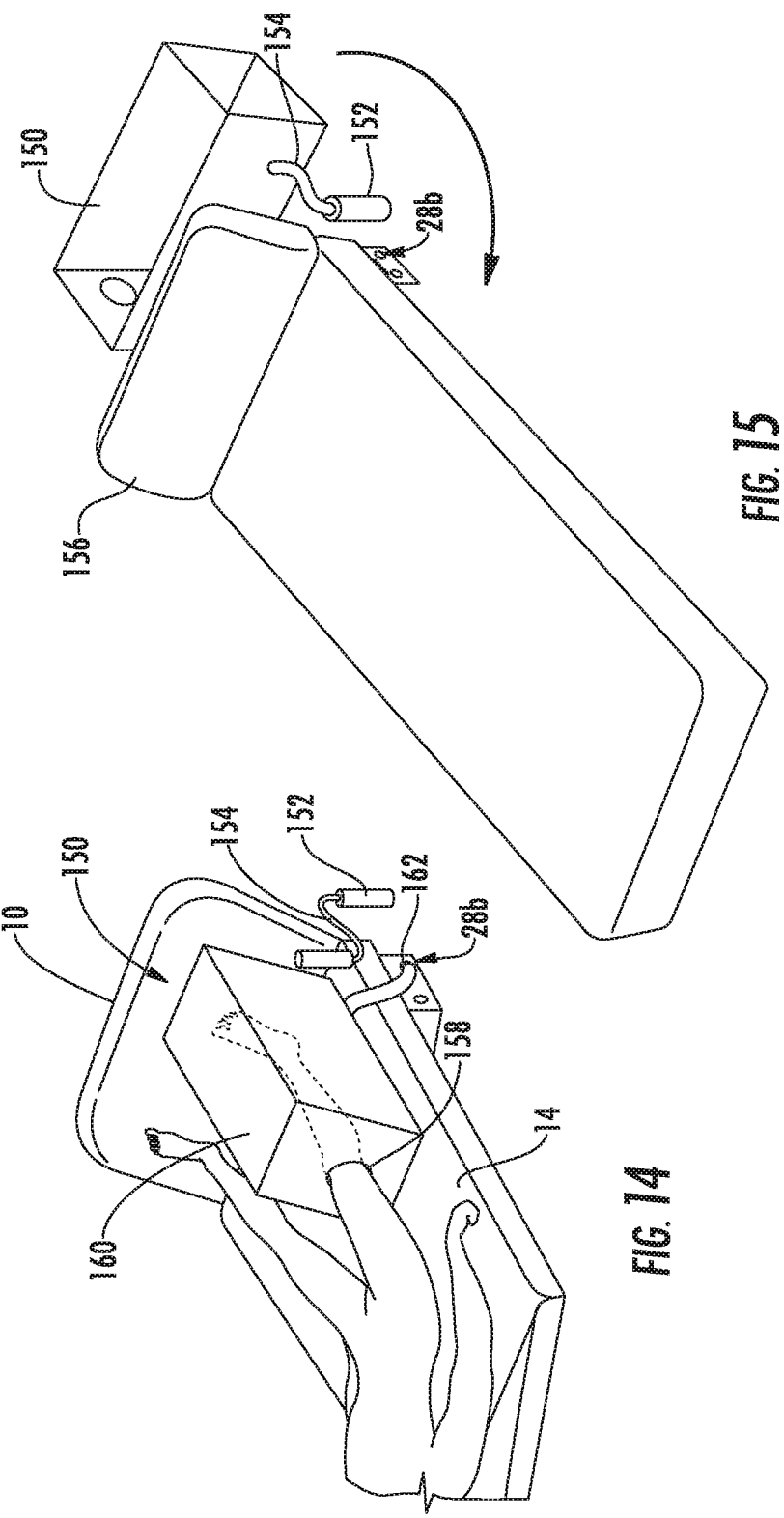

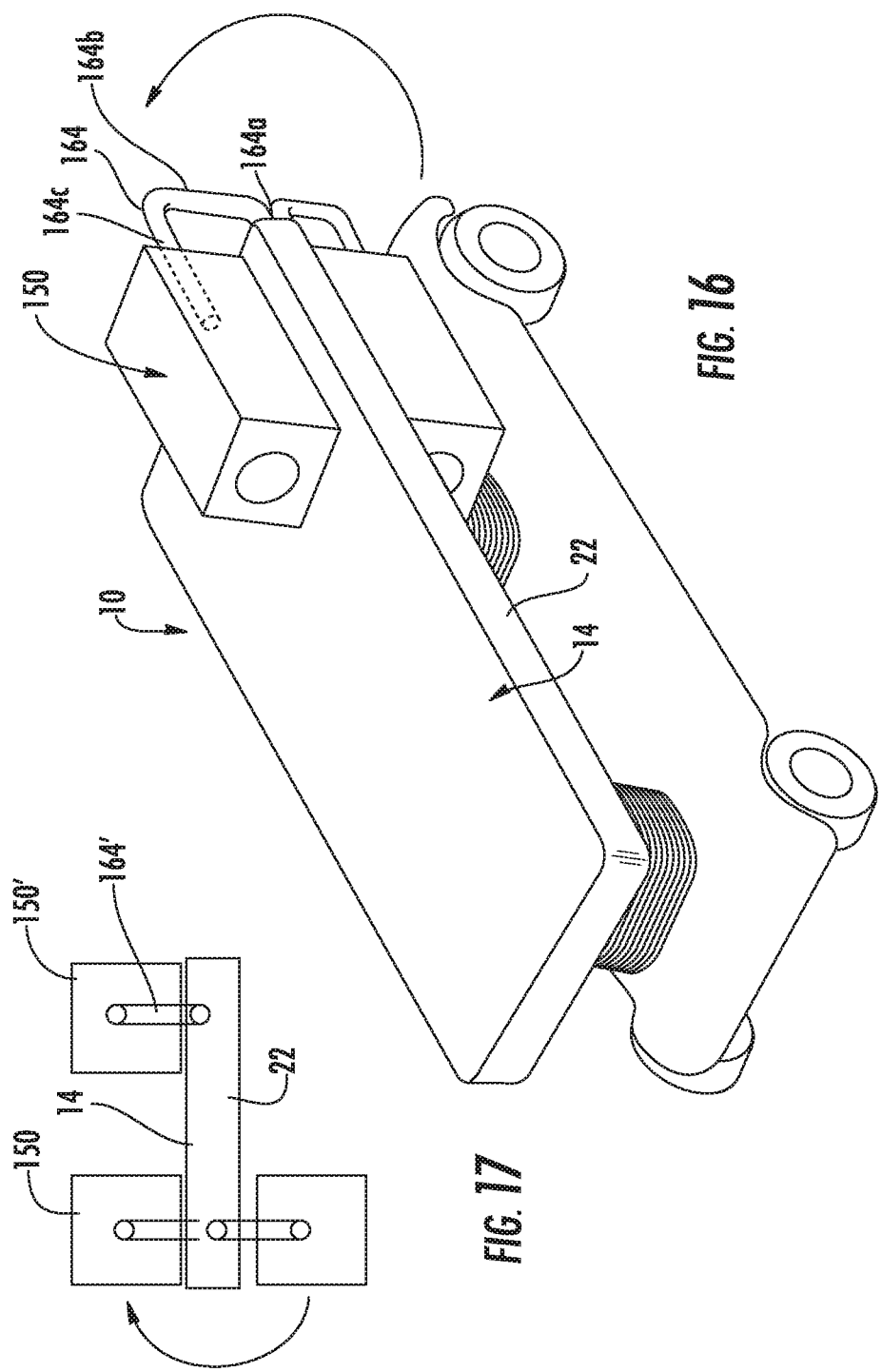

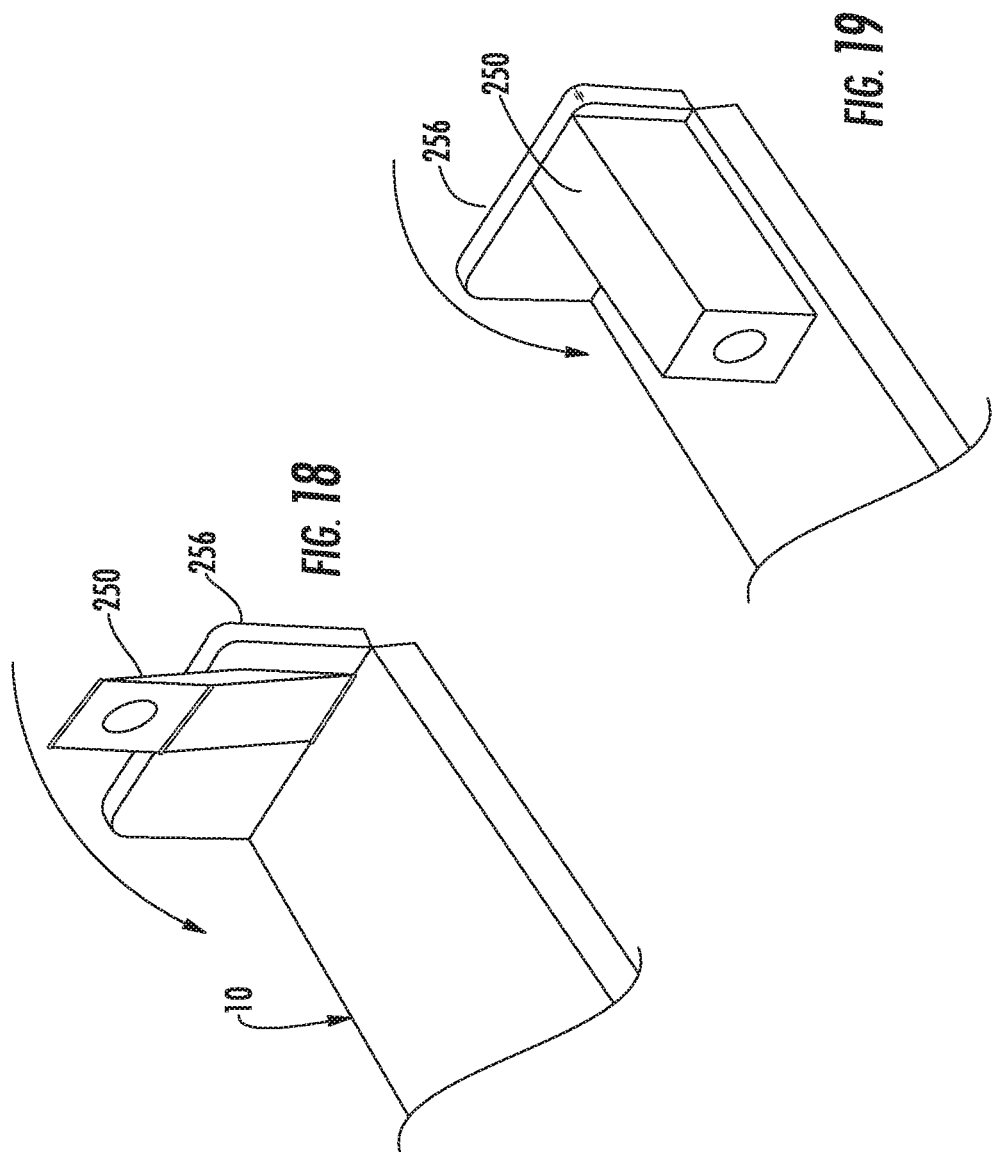

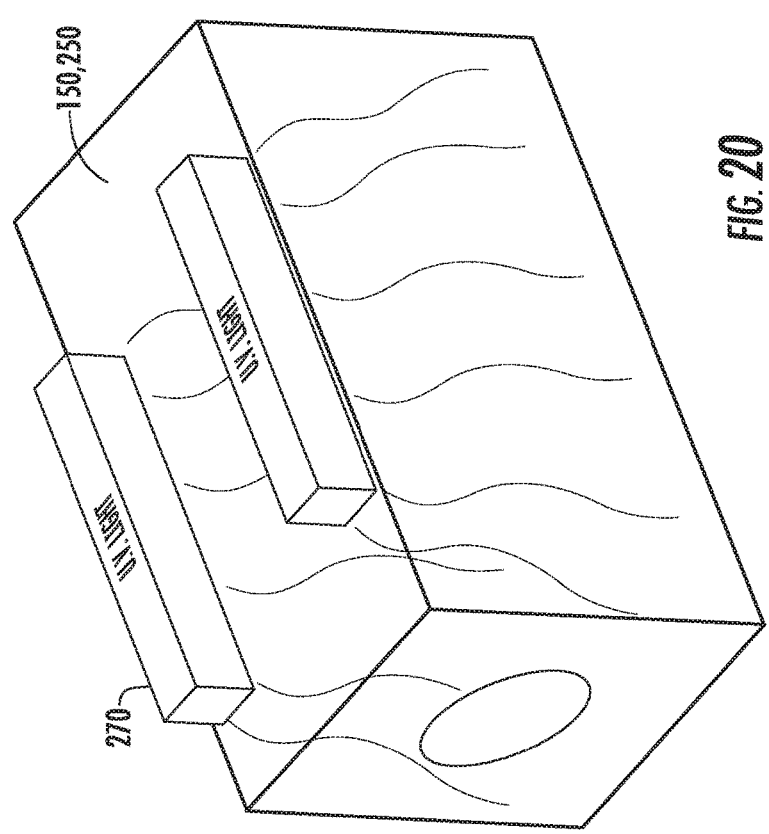

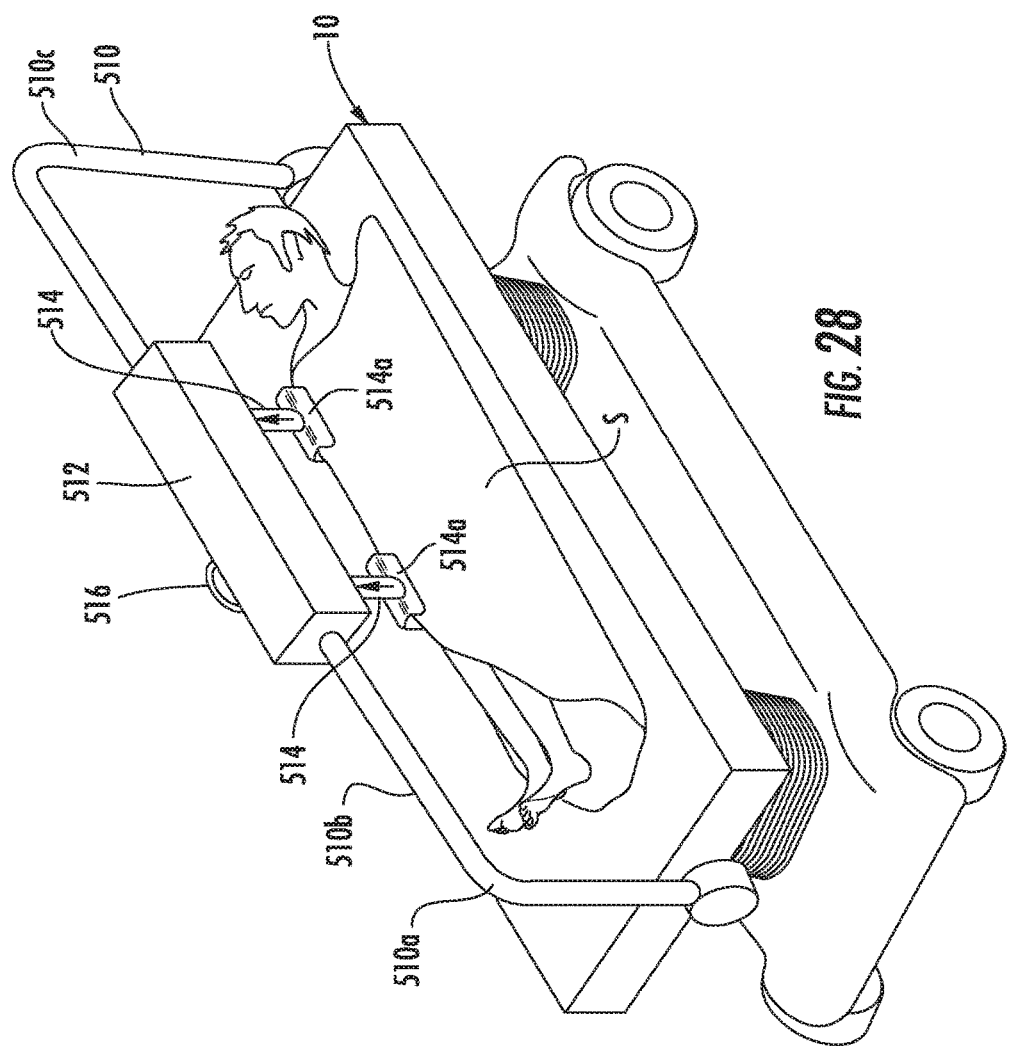

PATIENT SUPPORT WITH UNIVERSAL ENERGY SUPPLY SYSTEM

CROSS-REFERENCE TO RELATED APPLICATIONS

This application is a continuation of U.S. patent application entitled PATIENT SUPPORT WITH UNIVERSAL ENERGY SUPPLY SYSTEM, Ser. No. 14/549,226, filed Nov. 20, 2014, which is a continuation-in-part of U.S. patent application entitled PATIENT SUPPORT WITH UNIVERSAL ENERGY SUPPLY SYSTEM, Ser. No. 13/220,106, filed Aug. 29, 2011, which is a continuation-in-part of U.S. patent application entitled PATIENT SUPPORT WITH UNIVERSAL ENERGY SUPPLY SYSTEM, Ser. No. 12/057,941, filed Mar. 28, 2008, which claims the benefit of U.S. provisional application Ser. No. 60/923,501, filed Apr. 13, 2007, entitled UNIVERSAL ENERGY SUPPLY, and the benefit of U.S. provisional application Ser. No. 60/968,780, filed Aug. 29, 2007, entitled UNIVERSAL ENERGY SUPPLY, all of which are incorporated herein by reference in their entireties.

TECHNICAL FIELD AND BACKGROUND OF THE INVENTION

The present invention relates to a patient support and, more specifically, to a patient support that incorporates a universal energy supply system for delivering energy or healing fluids to one or more devices at the patient support for treating or caring for a patient.

SUMMARY OF THE INVENTION

According to the present invention, a patient support includes a patient support surface, a fluid movement system provided at the patient support, and an access port, which is also provided at the patient support and in selective fluid communication with the fluid movement system. The access port is adapted to couple to a pneumatic device that is selected from a group consisting of an inflatable device, a conduit, an air operated device, a pneumatic actuator, a ventilator, and a chamber, for delivering fluid to or suctioning fluid from the device when the device is coupled to the port.

In one embodiment, the fluid movement system is removable as a unit from the patient support. Optionally, the unit provides quick connect coupling so that the unit can be mounted in the patient support with one-click installation and similarly removed. Further, the unit may be functional independently of the patient support.

According to one aspect, the unit may include a housing that is configured to allow one-click installation so that the unit can be mounted into the support single handedly. For example, the housing may enclose a power supply for powering the fluid movement system and a control system. The housing may include one or more electrical contacts in communication with the control system and at least one pneumatic port in communication with the fluid movement system for directly or indirectly delivering fluid or suctioning fluid to and from the pneumatic device. The electrical contact(s) and pneumatic port are provided at the housing in a location that align with and allow for quick coupling to corresponding contacts and ports provided in the patient support.

For example, the patient support may include a patient support power supply system and a recess with an electrical connection in communication with the patient support power supply system for coupling to the power supply of the unit to the patient support power supply system, when the unit is mounted in the patient support, to recharge the battery and/or to allow the fluid movement system to be powered directly from the patient support power supply system instead of the unit's battery.

The patient support may include a recess with a pneumatic port for communicating with the pneumatic port at the housing that couples to or is coupled to the access port, which may be located adjacent or near the patient support surface (e.g. mattress) of the patient support so that fluid or suction from the unit can be directed from the pneumatic port of the unit to the access port at the patient support for coupling to the pneumatic device.

According to yet another aspect, the patient support includes a controller, and the unit includes controls for controlling the operation of the fluid movement system. Optionally, the controller of the patient support is in communication with the controls of the unit so that the controller of the patient support may operate the unit at least when the unit is mounted at the patient support and coupled to the controller of the patient support. For example, the unit may include one or more data ports that allow for physical coupling of the unit's control system to the controller of the patient support when the unit mounted in the patient support.

Alternately or in addition, the patient support and the unit may each include wireless communication electronics, such as a transceiver (or a receiver and transmitter) to allow the unit to communicate wirelessly with the controller of the patient support when the unit is mounted in the patient support or when the unit is in close proximity to the patient support. The wireless communication devices may comprise near field wireless communication devices.

In a further example, the patient support may include other communication electronics, such as a transceiver (or a receiver and transmitter) to allow the patient support to communicate with a device that is remote from the patient support, for example a network, including a hospital network, a nurse call station, or a medical records management system. Further, when the unit is in communication with the patient support, the communication electronics of the patient support may be configured to send data or other signals from the unit to the remote device so that the patient support becomes a communication hub for the unit.

In one example, the unit is operable to send information about itself to the patient support, which can then send the unit's information to the remote device for maintenance, protocol tracking, historic usage etc.

For example the unit may generate warnings or alerts, visual or audio, which then may be transmitted by the patient support to the remote device and/or displayed or sounded locally at the patient support. For example, the patient support may include a display with the warnings or alerts displayed at the display.

In one embodiment, the unit's controls are in communication with one or more sensors provided in the unit and/or connector that connects the pneumatic device to the unit. Further the controls are configured to detect a fault or alarm condition in the unit and/or connector, which can then be communicated to the patient support controller for either local or remote reporting.

In a further example, the patient support may include a monitoring system. The monitoring system may be configured to monitor the status of the unit and further configured to generate reminders to caregivers about the use of the unit.

According to yet another embodiment, either the patient support or the pneumatic device may include a sensor to detect if the pneumatic device is being decoupled, for example, when a patient is wearing the pneumatic device and tries to exit the patient support. Optionally, the sensor is in communication with either the patient support controller or the unit's controls, which generate an alert signal. For example the alert signal may be communicated to the patient support from the unit or communicated from the patient support to a remote device, such as a network, a nurse call station, or the like. In this manner the alert signal may be used to prevent damage to the pneumatic device and/or warn when there is potential exit by the patient from patient support.

In any of the above, the fluid movement system may form a DVT pump assembly for delivering fluid or suctioning fluid to and from a DVT device. In one embodiment, the DVT pump assembly is enclosed in a DVT pump assembly housing. For example, as noted above, the housing may be removably mounted in the patient support so that it can be replaced, repaired, or transported, for example, with a patient leaving the patient support.

According to one aspect, the DVT pump assembly housing may be configured to allow one-click installation so that the assembly can be mounted into the support single handedly. For example, the DVT pump assembly housing may include a pump and a power supply for powering the pump, as well as control circuitry, with one or more electrical contacts, for controlling the pump, and at least one pneumatic port in communication with the pump for directly or indirectly delivering fluid or suctioning fluid to and from the DVT device. The electrical contact(s) and pneumatic port are provided at the housing in a location that align with and allow for quick coupling to corresponding contacts and port(s) provided at the patient support.

For example, the patient support may include a patient support power supply system and a recess with an electrical connection in communication with the patient support power supply system for coupling to the power supply of the DVT pump assembly to the patient support power supply system to recharge the battery and/or to allow the pumps to be powered directly from the patient support power supply system instead of the battery.

The patient support may include a recess with a pneumatic port for communicating with the pneumatic port at the housing and which couples to or is coupled to the access port, which may be located adjacent or near the patient support surface (e.g. mattress) of the patient support so that fluid or suction from the DVT pump assembly can be directed from the pneumatic port of the DVT pump assembly to the access port at the patient support for coupling to the DVT device.

According to yet another aspect, the patient support includes a controller, and the DVT pump assembly includes controls for controlling the operation of the pumps. Optionally, the controller of the patient support is in communication with the controls of the DVT pump assembly so that the controller of the patient support may operate the DVT pump assembly at least when the DVT pump assembly is mounted at or is in close proximity to the patient support. For example, the DVT pump assembly may include one or more data ports that allow for physical coupling of the DVT pump assembly controls to the controller of the patient support when the DVT pump assembly is mounted in the patient support.

Alternately or in addition, the DVT pump assembly may include wireless communication electronics, such as a transceiver (or a receiver and transmitter) to allow the DVT pump assembly to communicate wirelessly with the controller of the patient support when the DVT pump assembly is mounted in the patient support or when the DVT pump assembly is in close proximity to the patient support.

In a further example, the patient support may include communication electronics, such as a transceiver (or a receiver and transmitter) to allow the patient support to communicate with a device that is remote from the patient support, for example a network, including a hospital network, a nurse call station, or a medical records management system. Further, when the DVT pump assembly is in communication with the patient support, the communication electronics of the patient support may be configured to send data or other signals from the DVT pump assembly to the remote device so that the patient support becomes a communication hub for the DVT pump assembly.

In one example, the DVT pump assembly is operable to send information about itself to the patient support, which can then send the DVT pump assembly information to the remote device for maintenance, protocol tracking, historic usage etc.

For example, the DVT pump assembly may generate warnings or alerts, visual or audio, which then may be transmitted by the patient support to the remote device and/or displayed or sounded locally at the patient support. For example, the patient support may include a display with the warnings or alerts displayed at the display.

In one embodiment, the DVT pump assembly controls are in communication with one or more sensors provided in the DVT device and/or tubing or hoses that connect the DVT device to the pump assembly. Further, the controls are configured to detect a fault or alarm condition in the DVT device and/or tubing or hoses, which can then be communicated to the patient support controller for either local or remote reporting.

In a further example, the patient support may include a monitoring system. The monitoring system may be configured to monitor the status of the DVT pump assembly and further configured to generate reminders to caregivers about the use of the DVT pump assembly.

According to yet another embodiment, either the patient support or the DVT device may include a sensor to detect if the DVT device is being decoupled, for example, when a patient is wearing the DVT device and tries to exit the patient support. Optionally, the sensor is in communication with either the patient support controller or the DVT pump assembly control, which generates an alert signal. For example, the alert signal may be communicated to the patient support from the DVT pump assembly or communicated from the patient support to a remote device, such as a network, a nurse call station, or the like. In this manner the alert signal may be used to prevent damage to the DVT device and/or warn of the potential exit by the patient from patient support.

Alternately or in addition, the patient support may include a quick disconnect between the DVT device connection to the port on the patient support to prevent tripping when a patient is exiting the patient support while still wearing the DVT device. For example, the quick disconnect connection may be a magnetic or friction-based connection.

Further, when the quick disconnect connection is magnet based, the magnetic coupling at the connection may be controlled to release the magnetic coupling in response to a signal, for example, by a signal generated at the patient support or remote from the support. The signal may be a patient support exit signal, including a predictive exit signal.

In yet another embodiment, either the unit of the patient support may monitor the usage of the pneumatic device. For example, the pneumatic device may include an RFID tag, which when energized by an RFID tag reader will generate a signal, for example, which can be used either by the patient support controller or the unit's controls to indicate that the device is in use. A counter or timing circuit may be provided, which could keep track of the number of times or the length of time the device has been used.

Alternately, the patient support or unit may include a near field communication transceiver that is adapted to communicate with the pneumatic device if the device is positioned within a near field vicinity of the near field communication transceiver. The controller or controls communicate with the near field communication transceiver, and is adapted to associate the patient support or unit with the pneumatic device when the near field communication transceiver is able to communicate with the device. The association then can be tracked to track the usage of the device.

For example, tracking usage of the pneumatic device may be used to determine when the use of the device has reached or exceeds it recommended maximum life and/or may be used for billing purposes. Further, when the controller or controls determine that the usage of the device reached or exceeds it recommended maximum life, the controller or controls is configured to disable the use of the pneumatic device.

In another embodiment, the device that is inflated may include an air inflated mattress or pillow; air inflated side rail; a hose or conduit delivering a gas or air, for example, to dry off patient after bathing or accidental urination or to create an air or gas curtain; an air activated blood pressure cuff; an air activated massage device, including integrated or external devices, for massaging various parts of the body (e.g. legs) for comfort or other reasons (e.g. decubitus care); a suction hose for urine collection; air inflated body for rotation; "air bag" style system to mitigate patient falls; suction activated wound drainage; devices for irrigation of wounds; suction activated waste evacuation devices; air powered instruments for other purposes, such as air tools, air activated pumps, etc.; passive motion exercising (e.g. gatch) actuators; patient ventilators complete with filtered and pressure controlled air; patient motion sensing system; air chamber, zoned, patient bed exit system; body lift devices, such as an air inflated fowler device; air inflated segmented body lift (turning or rotating) for wound care access (e.g. decubitus ulcers); air mattress system to enable a lift for X-ray film insertion; air activated peristaltic patient transfer/repositioning system; air filled gravity assist (e.g. a ramp) patient transfer aid device; an inflatable patient chamber for uses such as bio-hazard isolation chamber with filtered air intake/exhaust; a chamber for treatment gases; an inflatable patient chamber for highly concentrated oxygen delivery for improved healing (i.e. a hyperbaric chamber); bead filled patient immobilization device; portable, disposable fluid containment; air filled pad with ability to do air flotation patient transfers; air filled pad delivering treatment gas, such as high oxygen content air or other beneficial substances, such as atomized drugs or other treatments to promote healing; an air filled pad with temperature controlled air for patient warming or cooling; a low air loss air filled pad with temperature controlled to prevent or cure decubitus ulcers, body temperature control, or just for comfort; an inflatable bathtub system for in-bed bathing, for chemical decontamination or for other specialized treatments; or a portable/disposable fluid containment device.

In yet another embodiment, the fluid movement system is configured to adjust a parameter at the access port based on the treatment being applied.

In one aspect, the patient support controller is configured to detect the type of the pneumatic device. For example, the control system may be configured to detect the device when the device is in close proximity to or coupled to the access port.

In a further aspect, the patient support surfaces may each comprise a frame and a mattress, with the port provided at the frame. Further, the patient support may have a plurality of access ports at spaced locations around the patient support so that a caregiver can access the fluid movement system from either side or end of the bed.

According to yet a further aspect, the patient supports may include a heating or cooling device for heating or cooling the fluid in the fluid movement system.

In other aspects, the patient supports may include a compressor for pressurizing the fluid in the fluid movement system so that the fluid movement system may deliver pressurized fluid. Optionally, with multiple ports, the fluid movement system may provide high pressure at one or more ports and low pressure fluid at one or more other ports. Additionally, the fluid movement system may include a vacuum line in selective fluid communication with the ports wherein the vacuum line provides suction at a respective port when the vacuum line is in fluid communication with the respective port.

According to yet another embodiment, the access port is adapted for delivering fluid or a vacuum pressure to the device when the pneumatic device is coupled to the port.

In one aspect, the fluid movement system is configured to couple to an external fluid supply. Optionally, an onboard fluid supply is provided at the patient support so that the control system can deliver fluid from either the external fluid supply or the onboard fluid supply. Further, the fluid movement system may be configured to couple to an external vacuum supply. Again, the patient support may optionally include an onboard vacuum supply. In this manner, the patient support can provide continuous care of a patient whether or not the patient support is coupled to an external vacuum or fluid supply.

In one aspect, the support includes a control system that is configured to detect the type of the device. For example, the port may be provided with a sensor, such as an RFID reader that detects an RFID tag associated with a device that is to be coupled to the energy supply system, with the RFID tag identifying the device and/or providing information about the device. Further, the control system is configured to control the pressure of the fluid in the fluid movement system to suit the device based on the information received by the RFID reader. In this manner, the patient support can adapt its energy supply system to suit the device that is coupled to the patient support.

In another aspect, the patient support surface comprises a frame and a mattress, with the port provided at the frame.

According to yet another embodiment, the patient support may incorporate a compartment or housing to store a supply of the inflatable devices. For example, the compartment or housing may be mounted beneath the patient support surface of the patient support, for example beneath the frame that supports the patient support surface, or in or at the footboard board, headboard, or one of the side rails.

In another form of the invention, a patient support is coupled to treatment chamber, which is configured to be moved from a storage position to a deployed position where the patient may be treated.

In any of the above, the patient support may incorporate line management features and/or other types for storage structures for storing the pneumatic devices and/or its accessories, for example, tubing or supplies of tubing and/or pneumatic devices.

It should be understood that any of the above energy supply systems may be used to supply energy to a variety of devices or systems, including: a DVT device; air inflated mattress or pillow; air inflated siderail; a hose or conduit delivering a gas or air, for example, to dry off patient after bathing or accidental urination or to create an air or gas curtain to protect the patient; air activated blood pressure cuff; an air activated massage device, including integrated or external devices, for massaging various parts of the body (e.g. legs) for comfort or other reasons (e.g. decubitus care); a suction hose for urine collection, such as on a fighter jet; air inflated body for rotation; "air bag" style system to mitigate patient falls; suction activated wound drainage; devices for irrigation of wounds; suction activated waste evacuation devices; air powered instruments for other purposes (air tools, air activated pumps, etc.); passive motion exercising (e.g. gatch) actuators; patient ventilators complete with filtered and pressure controlled air; patient motion sensing system; air chamber, zoned, patient bed exit system; body lift devices, such as an air inflated fowler device; air inflated segmented body lift (rotate) for wound care access (e.g. decubitus ulcers); air mattress system to enable a lift for X-ray film insertion; air activated peristaltic patient transfer/repositioning (boost) system; air filled gravity assist (ramp) patient transfer aid device; an inflatable patient chamber for uses such as bio-hazard isolation chamber with filtered air intake/exhaust; a chamber for treatment gases; an inflatable patient chamber for highly concentrated oxygen delivery for improved healing (hyperbaric chamber); bead filled patient immobilization device; portable, disposable fluid containment; air filled pad with ability to do air flotation patient transfers (air hockey); air filled pad delivering treatment gas, such as high oxygen content air or other beneficial substances, such as atomized drugs or other treatments (such as disclosed in U.S. Pat. No. 8,048,044, which is commonly owned by Stryker Corporation of Kalamazoo, Mich. and is incorporated by reference herein in its entirety, to promote healing; an air filled pad with temperature controlled air for patient warming or cooling; air filled pad with temperature controlled (hot/cold) air escaping toward the patient to prevent or cure decubitus ulcers, body temperature control, or just for comfort; an inflatable bathtub system for in-bed bathing, for chemical decontamination or for other specialized treatments; and a portable/disposable fluid containment device, for example.

Consequently, the present invention provides a patient support with universal application that can power or energize a variety of devices or deliver fluid to a device or to the patient to provide continuous care for a patient regardless of the condition of the patient or the location of the patient support.

These and other objects, advantages, purposes, and features of the invention will become more apparent from the study of the following description taken in conjunction with the drawings.

BRIEF DESCRIPTION OF DRAWINGS

The detailed description particularly refers to the accompanying figures in which:

FIG. 4 is a perspective view of the universal energy supply system of FIG. 3;

FIG. 5 is another perspective view of the energy supply system of FIG. 4;

FIG. 6 is a second bottom perspective view of the patient support of FIG. 1;

FIG. 7 is an enlarged perspective fragmentary view of the patient support of FIG. 6 illustrating the heating and cooling portion of the universal energy supply system;

FIG. 9 is a perspective view of an operating table with a fluid movement system of the present invention;

FIG. 10 is a schematic perspective view of a patient support incorporating an inflatable device, such as compartment or tent;

FIG. 11 is a perspective view of a patient support of the present invention incorporating a compartment or housing for holding disposable inflatable devices, such as disposable hyperbaric devices, inflatable vacuum assist closure devices, disposable patient transfer pallets or drug delivery devices;

FIG. 14 is a schematic perspective view of the patient support incorporating a chamber mounted to the patient support;

FIG. 15 is a similar view to FIG. 14 illustrating the chamber in a non-deployed position;

FIG. 16 is another schematic drawing of a patient support incorporating a movable chamber that is movable between a deployed position and a stored position;

FIG. 17 is an end elevation view of the patient support of FIG. 16 illustrating a second chamber incorporated at the patient support;

FIG. 18 is a partial perspective view of a patient support incorporating a chamber incorporated at the foot board of the bed;

FIG. 19 illustrates the chamber in a deployed position;

FIG. 20 illustrates a chamber of the present invention incorporating one or more devices to provide decontamination within the chamber;

FIG. 28 is a perspective view of a patient support of the present invention incorporating a frame with lifting devices that may be used to turn a patient;

FIG. 34A is a schematic pneumatic drawing of the universal energy supply system unit coupled to a garment when the universal energy supply system unit is on;

DETAILED DESCRIPTION OF THE INVENTION

Figure 1:
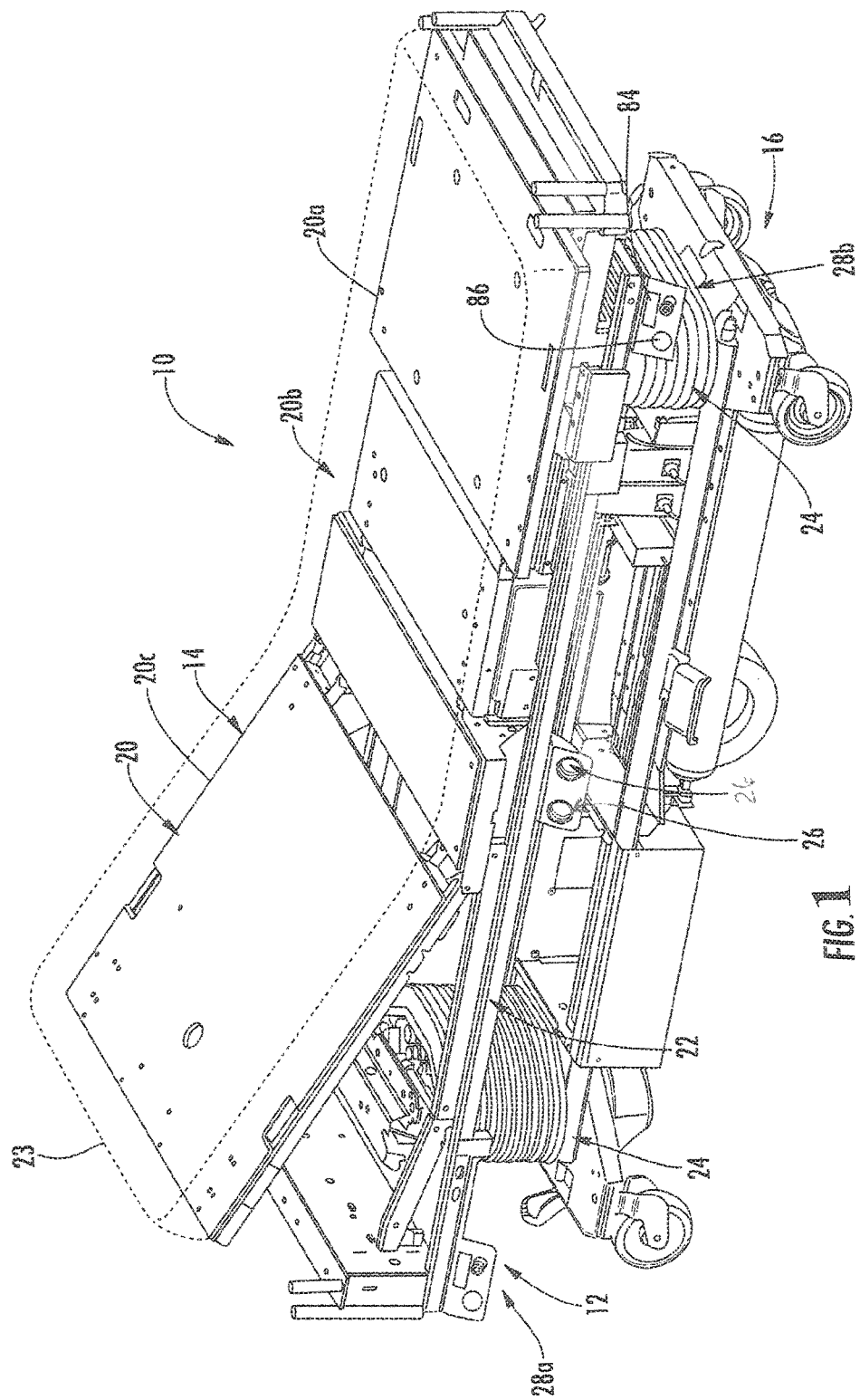
FIG. 1 is a perspective view of a patient support in the form of a hospital bed incorporating a universal energy supply system.

Referring to FIG. 1, the numeral 10 generally designates a patient support. As will be more fully described below, patient support 10 incorporates a universal energy supply system 12, which may deliver fluid or vacuum pressure to a plurality of discrete locations provided at the patient support so that various devices may be powered, actuated, used as a conduit, or the like at the patient support by the fluid or vacuum or so that a fluid or vacuum may be provided for treating or handling the patient. Further, universal energy system 12 may provide high pressure/low volume fluid or high volume/low pressure fluid, and further warmed or cooled fluid. The vacuum or fluid supply may be external to the patient support, with the energy supply system acting merely as a conduit and control system for the fluid or vacuum pressure. Alternately, or in addition, the universal energy supply 12 may have its own supply of vacuum pressure or fluid, which is provided at the patient support to provide a self-contained energy supply system so that a patient that is supported by the patient support can receive continuous care even when the patient support is disconnected from an external supply of fluid or vacuum. In addition, the electrically powered components of the system may be located beneath the patient support surface or at an underside of the patient support surface, with some for example, located in the base of the patient support, while the ports may be located at the patient support surface, which provide power without the attendant risks associated with electrical power. Further, the universal energy system therefore may provide energy in one form that can then be transformed into another form of energy, such as mechanical or pneumatic energy.

In the illustrated embodiment, patient support 10 comprises a bed; however, it should be appreciated that patient support 10 may comprise other patient supports including, for example, stretchers, cots, surgical tables, chairs, such as treatment recliners, physical therapy tables, wheel chairs, or the like. For ease of description, the following description will be made in reference to a bed, though it should be understood that the invention is not so limited. Further, the present invention may be incorporated into different types of beds, including a hospital bed, a long term facility care bed, or a bed in a home.

Figure 2:
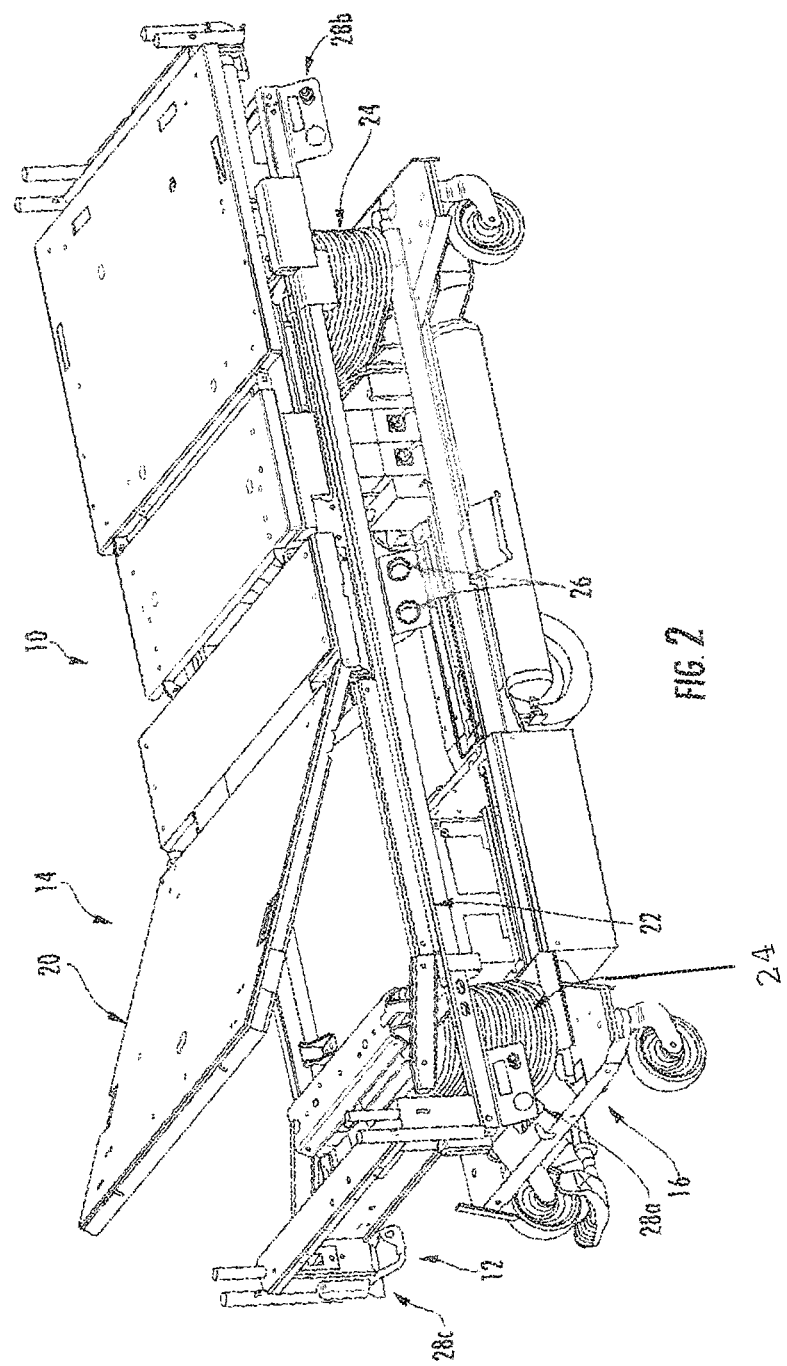
FIG. 2 is a second perspective view of the patient support of FIG. 1.

As best seen in FIGS. 1 and 2, patient support 10 includes a support surface 14 that is mounted to a base 16. In the illustrated embodiment, the base is a wheeled base supported on a plurality of casters; however, it should be understood that the patient support may include a fixed base, for example, in the case of a OR table. Support surface 14 includes an articulating deck 20, with a foot section 20a, a seat section 20b, and a head section 20c, which are supported by an intermediate frame 22. Support surface 14 further includes a mattress 23, which may comprise a foam mattress or a mattress with bladders, or a combination of both. For examples of suitable mattresses that may be supported on the deck, reference is made to U.S. Pat. Nos. 5,179,142; 7,784,125; 8,006333; 8,201,292 and copending applications U.S. patent application Ser. No. 11/381,631, filed May 4, 2006, entitled VIBRATING PATIENT SUPPORT APPARATUS WITH A RESONANT REFERENCING PERCUSSION DEVICE (which are commonly owned by Stryker Corporation of Kalamazoo, Mich. and incorporated by reference in their entireties herein. Further, for a maternity bed, a suitable mattress may include a mattress described in U.S. patent application Ser. No. 12/057,665, filed Mar. 28, 2008, entitled MATERNITY BED AND PATIENT LYING SURFACE THEREFOR (which is commonly owned by Stryker Corporation of Kalamazoo, Mich. and incorporated by reference in its entirety.

Intermediate frame 22 is movably mounted to base 16 by a pair of lift mechanisms 24 so that the support surface may be raised or lowered as desired. Suitable lifting devices for the frame include mechanical lifting devices, including screw lifts, or hydraulic jacks or cylinders, such as disclosed in U.S. Pat. Nos. 5,172,442; 6,820,294; and 7,150,056, which are commonly owned by Stryker Corporation of Kalamazoo, Mich. and which are incorporated by reference in their entireties herein. Further, the head and foot deck sections may be raised or lowered using actuators, such as disclosed in U.S. Pat. Nos. 7,690,059; 7,805,784; 7,962,981; and 7,861,334, all commonly owned by Stryker Corporation of Kalamazoo, Mich. and which are incorporated by reference herein in their entireties. It should be understood that energy supply system 12 may be incorporated into patient supports that have fixed patient surfaces as well as fixed bases, as noted above.

Referring again to FIGS. 1 and 2, energy supply system 12 includes a plurality of ports 26, 28a, 28b, 28c, and 28d, which are mounted at discrete locations at patient support 10, such as at or near the four corners of patient support 10, for providing a fluid or vacuum pressure at one or more ports. In this manner, the ports are provided at spaced locations around the patient support surface so that a user, such as a caregiver or patient, can access the energy supply system from either side or either end of the patient support. Further, it should be understood that multiple ports can be provided at each location to provide separate ports for fluid delivery and for the vacuum pressure.

Ports 26, 28a, 28b, 28c, and 28d are adapted to couple to various devices, which are either powered or actuated by the fluid or vacuum or provide a conduit for the fluid or vacuum for delivering the fluid or vacuum to another location on the bed, including to the patient and/or the patient support surface. For example, a conduit, such as a flexible hose, may be coupled to any one of the ports to deliver the fluid or vacuum to another device, such as nozzle, a DVT device, an irrigation tool, such as a lavage device, which is used for debridement of a wound, or to the mattress or the like, as will be more fully described below. In addition, as will be more fully described below, one or more of the ports may be used to direct air to a perforated conduit that directs air or gas flow near or over a patient to create an air or gas curtain to isolate the patient from the ambient air environment to reduce the chances of infection.

Figure 3:
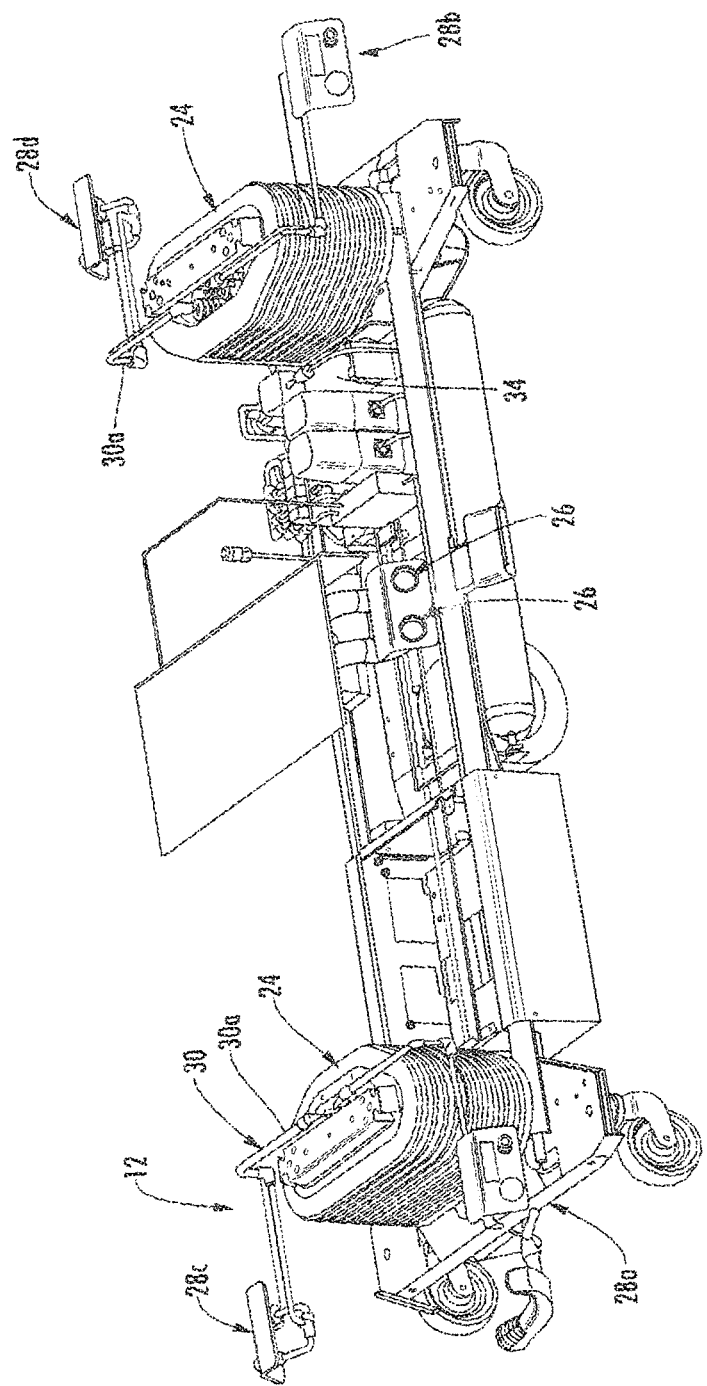
FIG. 3 is a perspective view of the patient support of FIGS. 1 and 2 illustrating the universal energy supply system with the patient support surface removed for clarity.
Figure 8A:
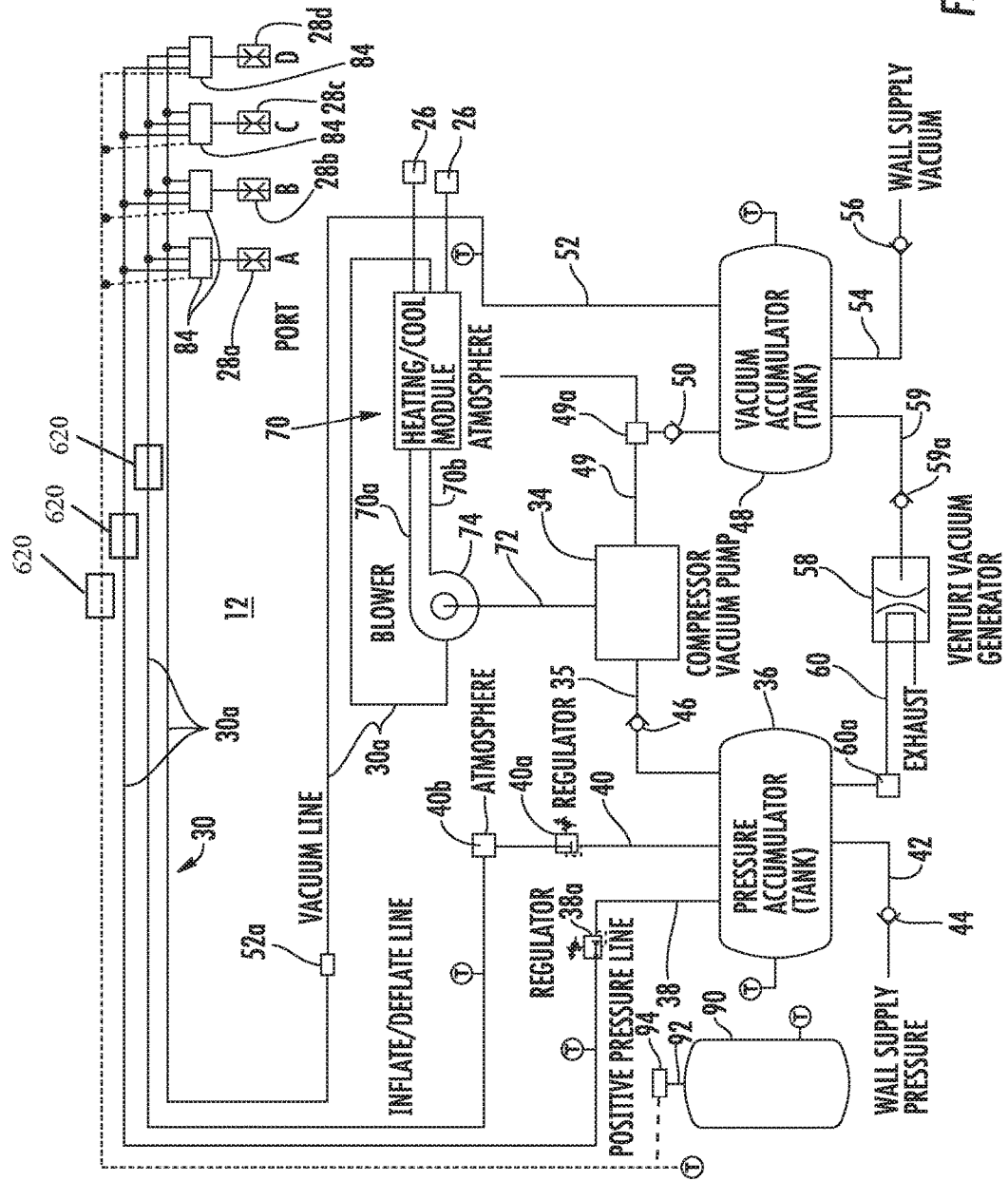
FIG. 8A is a schematic drawing of the universal energy supply system.
Figure 8B:
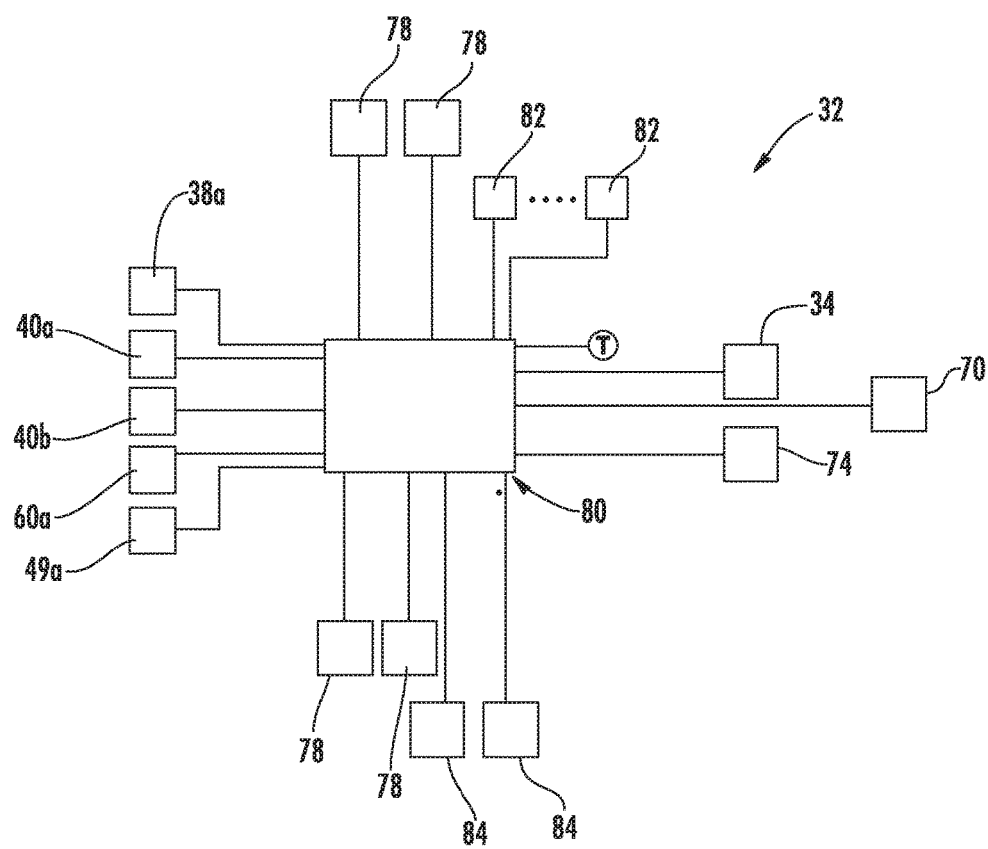
FIG. 8B is a schematic drawing of the control system of the universal energy supply system.

Referring to FIGS. 3-5, energy supply system 12 includes a fluid movement system 30 (FIG. 8A) and a control system 32 (FIG. 8B). Control system 32 controls fluid movement through fluid movement system 30 and, further, the fluid movement at the respective ports. Fluid movement system 30 includes tubing or conduit 30a that is in fluid communication with a fluid supply (either an onboard supply or an external supply or both) and is in selective fluid communication with the respective ports 26, 28a, 28b, 28c, and 28d to selectively deliver fluid or vacuum pressure to the respective ports. In the illustrated embodiment, tubing 30a comprises a three-cannula tube to provide three conduits or lines, namely a pressure line (38), an inflate/deflate line (40), and a vacuum line (52) (FIG. 8A). A fourth conduit or line may also be provided to deliver treatment fluid, such as a liquid or atomized liquid, to any one of or all the ports to allow treatment fluid to be delivered to a device or patient, also more fully described below. It should be understood that separate tubes may be run for each line and, further, additional lines or cannulae may be provided, for example, to provide additional conduits, such as a gas line, including as noted a treatment fluid or gas line, for example an oxygen line, more fully described below.

As best seen in FIG. 3, tubing 30a runs through the patient support, and is supported at various points, for example in the base 16, and further extends through the respective lift assemblies 24 and thereafter extends to the respective ports 28a-28d and 26. To accommodate the vertical movement of the patient surface relative to the base, tubing 30a may include coiled sections 30b, which accommodates the relative movement of the lower portion of the tubing relative to the upper portion of the tubing resulting from any adjustment in height of the patient support surface relative to base 16.

In the illustrated embodiment, fluid movement system 30 may operate as a fluid delivery system, including a high pressure/low volume or a high volume/low pressure, and/or as a vacuum system. As used herein, the term "fluid" includes liquid and/or a gas, such as air and may include gases, such as treatment gases, for example oxygen, or mixtures thereof, which will be more fully described below. For example, in the illustrated embodiment, ports 28a-28d may be configured to deliver high pressure/low volume fluid or a vacuum pressure, while ports 26 may be configured to deliver low volume/high pressure fluid.

Referring to FIG. 8A, fluid movement system 30 optionally includes a compressor/vacuum pump 34, which delivers pressurized air to a pressure accumulator 36. The compressor/vacuum pump may be onboard, as noted, or may comprise an external compressor/vacuum pump, which delivers pressurized air (or a vacuum as noted below) to a pressure accumulator 36. Pressure accumulator 36 is in fluid communication with pressure line 38 and an inflate/deflate line 40, which are respectively in fluid communication with respective ports 28a-28d. The flow of fluid through lines 38 and 40 is controlled and regulated by pressure regulators 38a and 40a, respectively, which are also controlled by control system 32. Further, pressure accumulator or tank 36 includes a conduit or line 42 for coupling to a wall supply pressure through a check valve 44. As noted, the compressor may be external to the patient support and may be coupled to the wall supply pressure.

Compressor/vacuum pump 34 is in fluid communication with pressure accumulator 36 through a check valve 46 and also in communication with a second tank or vacuum accumulator 48 through conduit or line 49 and through check valve 50. Tank 48 is in fluid communication with vacuum line 52, which is in selective fluid communication with respective ports 28a-28d to provide vacuum pressure at the respective ports and so that a vacuum pressure may be selectively provided at the respective ports. Again, as noted above, the compressor/vacuum pump may be on board or external to the patient support.

In addition, vacuum accumulator 48 optionally includes an external vacuum line 54, which is in fluid communication with a wall supply vacuum through a check valve 56. In this manner, both the fluid delivery system and the vacuum system may be coupled to sources external to the bed so that the energy supply system can be hooked up to, for example, a wall pressure supply or a wall vacuum supply when patient support 10 is in, for example, a hospital room. As will be more fully described below, in addition to an onboard fluid supply (tank 36), patient support may also incorporate an onboard vacuum generator.

As noted above, the vacuum pressure may be supplied by a wall vacuum supply or an onboard supply. As best seen in FIG. 8A, vacuum accumulator 48 may be in fluid communication with a venturi vacuum generator 58 through line 59 and check valve 59a. Vacuum generator 58 generates a vacuum pressure using a venturi effect generated by an exhaust line 60 that extends off tank 36. In this manner, when patient support 10 does not have access to an external vacuum supply, such as a wall vacuum supply commonly found in a hospital room, patient support 10 may still provide the necessary vacuum pressure to provide continuous care to the patient even though the patient support 10 may be in transit or not located near an external source.

As would be understood, therefore, ports 28a-28d may provide fluid in the form of a negative pressurized fluid (such as a vacuum pressure) or in the form of a positive (high or low) pressurized fluid, which, as noted above, may be used to power one or more devices at the patient support for the care, handling, treatment or monitoring of a patient supported at patient support 10. Further, in order to control the pressure in the respective lines of fluid movement system 30, control system 32 includes sensors, for example pressure transducers T, that may be provided at various locations, such as at tanks 36, 48, at lines 38, 40, and 52 and also at supply tank 90 and line 92 (FIG. 8A). Sensors (T) are in communication with controller 80 of control system 32, which monitors the pressure at the various locations to provide pressure feedback for system 32.

In addition, energy supply system 12 may incorporate a heating and/or cooling device 70 for heating or cooling the fluid in fluid movement system 30. In the illustrated embodiment, fluid is delivered from compressor 34 through a conduit 72 to a blower 74, which circulates the fluid through the heating and/or cooling device 70, which either heats or cools the fluid. In this section of the fluid movement system, the conduits may have increased diameters to facilitate the transfer of heat to the fluid, which forms a high volume/low pressure fluid supply. To access this lower pressure/high volume supply of warm or cold fluid, ports 26 are provided at frame 22 and coupled to and in fluid communication with the respective warm and cool lines, which also provide connections for various devices to the patient support. It should be noted that the blower may be similarly provided external to the patient support.

As best seen in FIGS. 6 and 7, blower 74 and heating and/or cooling device 70 may be supported beneath patient support surface 14. And, as best understood from FIG. 4, compressor/vacuum pump 34, pressure accumulator 36, and pressure regulators 38a and 40a are all supported at base 16. Hence all the high voltage components are located beneath or below the patient support surface. While configured to be powered from a 110-volt supply, for example, a conventional electrical outlet, the electrical components of the energy supply system may be powered from the bed voltage supply, such a battery, including a rechargeable battery, and further by way of a toroid, such as disclosed in U.S. Pat. No. 7,690,059. As would be understood therefore, although the energy system is powered by electricity, the power supplied at the patient support surface may be in a non-electrical form and, hence, reduces the risk of exposing the patient to electrical contact while still providing power.

Devices that may be coupled to the respective ports include inflatable devices, such as air inflated mattresses or pillows or pads, including an air inflated fowler, an air inflated segment body lift for rotating a patient to provide wound care access, an air mattress system to enable a lift for an X-ray film insertion, an air filled gravity assist ramp that assists in transferring the patient, an inflatable patient chamber, which can be used as a biohazard isolation chamber with filtered air intake/exhaust, an inflatable patient chamber for treating a wound or for simply applying a medication or drug topically through the tissue, such as skin or an open wound, applying treatment gas (such as highly concentrated oxygen for improved healing, such as in hyperbaric chamber) or a vacuum or other beneficial substances, such as a drug or the like to a patient, an air filled pad to create an air flotation patient transfer device, an air filled pad that may be used to deliver or apply treatment gas, for example, oxygen, or other beneficial substances or a vacuum to treat a wound or other condition to promote healing (like a hyperbaric chamber), an air filled pad with temperature controlled air for patient warming or cooling, an air activated cuff, an air filled pad with temperature controlled air escaping to the patient to prevent or cure decubitus ulcers, body temperature control, or just for comfort, an air inflatable bathtub system for in-bed bathing for chemical decontamination or for other specialized treatments, an inflatable chamber used for cleaning a patient's wounds such as by a lavage device, or an air inflated side rail, or the like.

As noted above, the energy system of the present invention may be used to power the patient surface, in the form of supplying air. For example, the energy support system 12 may supply pressurized air to a sequential valve system or to a pressure mapping feed back system for sequential inflation or deflation of the surface, such as a DVT device. Further, this may be done manually or automatically. As noted above, the patient surface may comprise a multiple segment mattress and/or include one or more inflatable bladders for turning the patient, for applying vibration and/or percussion treatment to prevent bed sores, to provide respiratory treatment, for retarding development of decubitis ulcers, or the like, such as disclosed in U.S. Pat. Nos. 5,179,142, 7,784,125; 8,006,333; 8,201,292; and 5,325,551; and copending U.S. patent application Ser. No. 11/381,631, filed May 4, 2006, entitled VIBRATING PATIENT SUPPORT APPARATUS WITH A RESONANT REFERENCING PERCUSSION DEVICE (or for delivery of warm to a patient warming apparatus incorporated into the surface, such as disclosed in U.S. Pat. No. 5,251,347, all commonly owned by Stryker Corporation of Kalamazoo, Mich., and all of which are incorporated by reference in their entireties herein.

For example, when energy supply system 12 is used to supply air to the inflatable bladders described in the vibration/percussion treatment surfaces referenced above, high volume/low pressure air or high pressure/low volume may be directed into the surface. When high pressure/low volume air is supplied, the pump described in the referenced patent and applications therefore may be eliminated provided that sufficient air pressure is supplied by the energy supply system 12 to the manifold, which delivers the air to the respective bladders. Similarly, the pump in U.S. Pat. No. 5,325,551 may also be eliminated provided sufficient air pressure may be supplied. With reference to the patient heating apparatus, the blower and/or heater may be eliminated should the air flow and temperature control provided by energy supply system 12, for example through ports 26, be sufficient.

As noted above, energy supply system 12 may also be configured to supply treatment fluid, such as fluid with a drug. It should be understood that the term "drug" is used broadly to include pharmaceuticals, including pain killers, such as opiates or steroids; hormones, such as androgens and estrogens, peptide hormones such as insulin, as well as performance enhancing drugs, such as steroid hormones; proteins, including morphogenetic proteins, such as bmp-2 and bmp-7; nutrients; antibiotics, such as tetracycline, penicillin, amoxicillin, erythromycin, for example; herbal medicine; vitamins; or other treatments. Further, when using the term "drug" or "drugs" it should be understood that this also includes any carriers, such as solvents or excipients, which may be added to the drug to aid in the delivery of the drug as well as enhance penetration or efficacy of the drug. For further details of how the drug may be delivered and applied using a topical pad or chamber, reference is made herein to U.S. Pat. No. 8,048,044, which is herein incorporated by reference in its entirety.

Other devices that may be mounted or coupled to the ports include delivery mechanisms, such as conduits, or air powered instruments, such as air powered tools or air activated pumps, etc. For example, the high pressure/low volume air supplied by energy supply system 12 may be used to drive the impeller on an air powered device, such as a tool or drive piston driven device to thereby power the device. In this manner, the energy from energy supply system 12 is transformed into mechanical energy. These devices may be directly coupled to the port or may be coupled to the port via a conduit. Conduits may be coupled to a port to deliver fluid or a vacuum pressure to another device or simply direct the fluid or vacuum to an applicator, such as a nozzle, including a lavage device, or direct the fluid or vacuum directly to the patient for treatment or care. For example, healing liquids or gases (such as liquids or gases, including medication or drugs, including liquids or gases with antibacterial properties or cell regeneration properties) may be directed to the patient using a conduit. Other applications include: suction hoses for urine collection, a conduit for delivering temperature controlled air to dry off a patient after bathing or accidental urination, air activated external massage device for various parts of the body for comfort and other reasons (e.g. decubitus care), a conduit for suctioning waste, a conduit for use as a power source for irrigation of wounds, a conduit for delivering air for use as a patient ventilation system, or the like.

Further, control system 32 is optionally adapted to detect the presence of a device either when the device is coupled to the port or when the device is in close proximity to the port. For example, close proximity to the port may include the device being within a range of 0-12 inches, or 0-6 inches, or 0-3 inches to the port. Each port 28a-28d may include a sensor, such as an RFID reader 78, which reads an RFID tag applied to the respective device. The RFID tag may contain an identification code for the device or contain information about the device, for example, the pressure requirements to operate the device, such as minimum pressure requirements and/or maximum pressure requirements. In this manner, based on the information conveyed by the RFID tag, control system 32 may determine the appropriate pressure needed for the device (such as by a look-up table stored in the control systems memory device, which may include one or more parameters for a plurality of devices or simply based on the information provided by the tag) and then adjust the pressure of the system and deliver the appropriate pressure to the port to which the device is attached. Alternately, control system 32 may be configured to supply pulsed fluid or a steady stream of fluid so that the control system 32 may be used to control the device rather than just simply providing energy in the form of pressurized fluid to the device and with the device controlling the use of the fluid. Consequently, the control system 32 may be configured to control the device and determine how the device will operate. In other words, a device may be coupled to the energy supply system with its output controlled by the control system 32.

As noted, control system 32 controls the level of pressure in the fluid movement system 30. As noted above, each of the positive pressure line 38 and the inflate/deflate line 40 includes a respective regulator 38a, 40a that is in communication with and controlled by control system 32, which includes a central controller or central processing unit 80. Central processing unit 80 is in communication with the regulators as well as the respective RFID readers 78 provided at the ports. In this manner, when the RFID reader reads the RFID tag of the respective device, the RFID reader, which is in communication with the central processing unit 80, will generate a signal that indicates the identification of the device or a pressure range or pressure required by the respective device. In turn, the central processing unit 80 will adjust the pressure in the appropriate line (38 or 40) through regulators 38a and 40a to provide an automatic system. For example, central processing unit 80 may be mounted adjacent one of the ports or may be mounted in the base, a side rail, a footboard or a headboard.

Alternately or in addition, control system 32 may provide for manual input. For example, central processing unit 80 may be coupled to a user input device, such as a keypad, touch screen or the like, so that a user, such as a healthcare provider, may select which port is to be used and to input the type of device that is to be coupled to the port. This may be achieved through the use of an icon, for example, an icon for each port, and/or through the use of a menu, for example a menu of the ports and/or a menu for devices that may be coupled to the ports. Further, the user input device may include buttons, such as a keypad, to allow the user to select the pressure, the type of flow, e.g. pulsed flow or constant flow, the frequency of the pulsed flow, or a profile for the pulse flow. In addition, the user input device may allow the user to select a duration for the flow of fluid or the temperature of the fluid. For example, the user input may be located at or near one of the ports and/or located in a siderail, headboard or footboard. Examples of suitable user input devices and examples of suitable buttons, menus, and touch screen displays that may be used to provide a user interface, reference is made to U.S. Pat. Nos. 7,690,059; 7,805,784; 7,962,981; 7,861,334; and 8,544,126 all commonly owned by Stryker Corporation of Kalamazoo, Mich. and which are incorporated by reference herein in their entireties.

Alternately, pneumatic-based user interfaces may be used. For example, air buttons that actuate switches using air, such as "sip& puff" controls, may be used to select functions or to control the operation of devices coupled to the ports via the controller. These controls may provide simple on/off functions or may provide selections between a menu of functions. Further, voice activated controls may be incorporated into central processing unit 80 so that the user may simply command the controller what functions are to be performed. Additionally, remote control may be used to control central processing unit 80. For example, central processing unit 80 may be coupled using a link to a remote nurse's station or to a remote location, including a remote location that is remote from the hospital or institution where the patient support is located. The link may be a hardwired link, such as an RS 232 cable, or a wireless link, including radio frequency or infrared frequency wireless transmission, in which case central processing unit 80 would include a receiver or a transceiver to allow the wireless communication. For example, where the energy supply system supplies fluid, for example, to a ventilator, the supply of fluid to the ventilator may be controlled remotely via central processing unit 80. Further, a data link between the ventilator and the controller may be provided, which transmits data from the ventilator to the central processing unit 80, so that the ventilator may be remotely monitored and controlled.

As noted above, the devices that may be included at a patient support include hyperbaric treatment devices or vacuum assist closure devices, including hyperbaric or vacuum assist closure chambers, which may be inflatable devices, and, further, which may be incorporated into the patient support described more fully below. For example, suitable hyperbaric or vacuum assist closure devices are described in U.S. Pat. Nos. 5,154,697; 5,636,643; 4,969,880; and 5,645,081, which are incorporated by reference herein in their entireties.

Referring to FIG. 8B, central processing unit 80, which is in communication with pressure regulators 38a, 40a and RFID readers 78, is also in communication with compressor 34. Further, central processing unit 80 is in communication with valves 40b, 52a, 60a, 49a, and 94 to control the movement of the fluid through the respective lines. In addition, central processing unit 80 is in communication with displays 82 (FIG. 5), such as LCD display, which may be provided at or near ports 28a-28d and used to display the type of device that is coupled to the respective port, the pressure being delivered by the system to the respective port, or other information related to the port. In addition, central processing unit 80 is in communication with blower 74 and heating/cooling module 70 to thereby control the heating and cooling of the fluid in fluid movement system 30.

Optionally, system 12 may also include an oxygen supply 90, including an oxygen concentrator, which is in fluid communication with the respective ports 28a-28d through a line 92 and control valve 94, such as a solenoid control valve. Optionally, oxygen can be injected into line 92 to provide an increased oxygen level or may be injected into line 92 to provide about 100% oxygen at a selected port for delivery to the patient, for example, through a respirator or for use in a hyperbaric treatment chamber for treatment of a patient's wound, as more fully described below. Central processing unit 80 is therefore also in communication with valve 94 to control the flow of oxygen in line 92. Further, system 12 may incorporate a humidifier in any one of lines 38, 40 and 92, which may be particularly suitable for use with a hyperbaric treatment device or drug delivery device.

In operation, central processing unit 80 controls the pressure in the fluid delivered to the respective port by regulating the pressure through regulators 38a and 40a. Further, central processing unit 80 is in communication with control devices 84 at the respective ports, which control whether constant pressurized fluid or an on/off pressurized fluid or oxygen is delivered to the respective port or whether a vacuum pressure is delivered to the respective port. For example, a suitable control device may include a three-way valve in the case of the three line system or a four way valve in the case of a four line system. Suitable three or four way valves include solenoid valves or a solenoid manifold. In this manner, when the central processing unit detects that a device requires a certain pressure at a respective port, the control unit will configure the fluid movement system to supply the appropriate pressure or vacuum at the respective port. Optionally, each port may include a pressure gage 86, which detects and indicates the pressure at the respective port.

Referring to FIG. 9, the numeral 10' designates another embodiment of a patient support in the form of a surgical or OR table. Patient support 10' similarly includes a support surface 14' that is mounted to a base 16'. Support surface 14' includes a plurality of articulating sections 20', with a foot section 20a', a seat section 20b', and a head section 20c', which are cantilevered from base 16' by a pedestal 24'. Optionally, pedestal 24' is a telescoping pedestal, which allows the patient support surface to be raised or lowered by way of actuators (not shown). Support surface 14' further includes a plurality of pads, such as a leg pad, a torso pad, and a head pad, which may comprise foam pads or pads with bladders or a combination of both.

Mounted at spaced locations around support surface 14' are a plurality of ports 28a', 28b', and 26', which provide fluid flow, including pressurizing fluid flow or a vacuum pressure, in a similar manner to the ports described above in reference to patient support 10. Ports 28a', 28b', and 26' are coupled to a fluid movement system and/or a vacuum system, and controlled by a control system similar to the systems described above; therefore, reference is made to the first embodiment for further details of the energy supply system of patient support 10'. It should be understood that the various component of the fluid movement system and/or a vacuum system maybe similarly supported and located in base 16' and further below the patient support surface 14' to again provide a system that can deliver energy at or near the patient support surface without the attendant risks associated with electrically powered devices.

Referring to FIG. 10, as noted above, patient support 10 may power an inflatable device. As best seen in FIG. 10, one example of an inflatable device includes an inflatable chamber or tent 100, which may be provided to form a shield and to retain splashes, for example from an irrigation tool, such as a pulsating lavage device 102. Suitable lavage devices are described in U.S. Pat. Nos. 4,278,078; 6,099,494; and 6,179, 807, all commonly owned by Stryker Corporation of Kalamazoo, Mich., which are incorporated by reference in their entireties.

For example, pulsating lavage device 102 may be coupled with one of the ports (28a-28d) at the patient support 10 and may be used to direct pulsating fluid onto a portion of a patient's body, for example through an opening 104 formed in the chamber 100. Optionally, chamber 100 may incorporate a boot that receives the tip of the lavage device but allows the tip to be maneuvered to properly treat the patient. For example, chamber 100 may be configured to receive a patient's leg or other extremities or the torso of the patient. Further, as noted above, chamber 100 may be coupled to another port on the patient support 10 through a conduit, such as tubing, to provide a source of pressurized air to inflate the chamber.

Referring to FIG. 11, chamber 100 or other inflatable devices, which will be more fully described below, may be incorporated or stored in a housing 110 mounted to patient support 10. For example, housing 110 may be mounted beneath the intermediate frame 22. Housing 110 optionally includes an access opening 112, which provides access to the disposable inflatable devices located in housing 110 and allows the dispensing of an inflatable device from housing 110. In this manner, when a caregiver wishes to utilize a disposable inflatable device, the device may be retrieved from housing 110 and then optionally coupled to the energy supply system 12 of patient support 10 to inflate the device or coupled to an external pressure supply. Further, the opening may allow the supply of inflatable devices to be replenished or recharged, or the housing itself may be removable for replacement with another stocked housing. While the housing is described and illustrated mounted to the intermediate frame, it should be understood that housing 110 may be located elsewhere on patient support, including in or on the footboard, side rail or head board.

Figure 12:
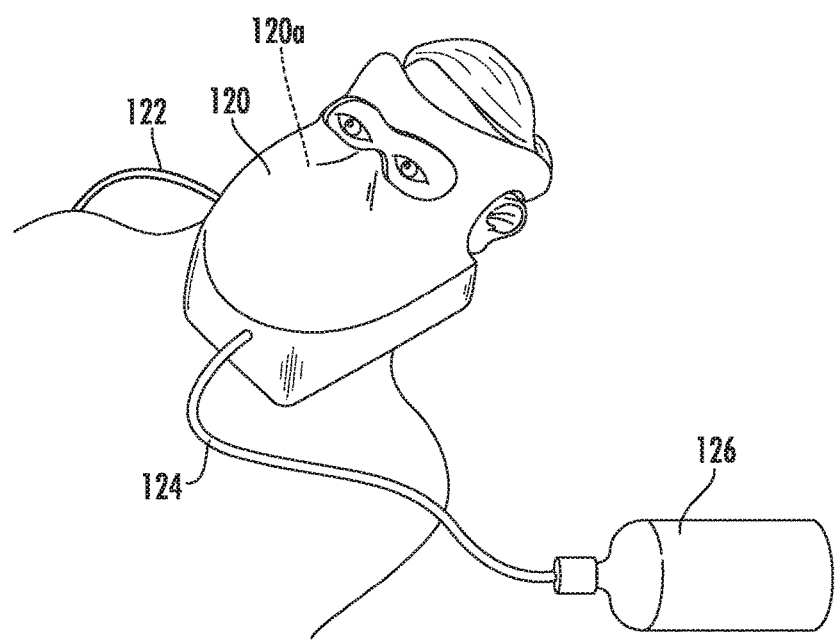
FIG. 12 is a perspective view of one embodiment of a disposable hyperbaric device.

For example, referring to FIG. 12, another suitable inflatable device may be configured as an inflatable mask 120. Mask 120 is configured to cover at least a part of a patient's face to provide treatment, such as vacuum assisted closure treatment or drug treatment or hyperbaric treatment to treat scars, for example scars from surgery. Mask 120 includes a cover, which is shaped to cover at least a portion of the patient's face and further form a chamber under the cover. A conduit 122 is coupled to the cover to inflate the cover. A suitable conduit 122 includes a tube, such a flexible tube, which may be coupled to energy supply system 12 of patient support 10 to inflate mask 120. Further, inflatable device 120 may include a second conduit 124, which is in fluid communication with the chamber for delivering a vacuum pressure or pressurized fluid, such as pressurized atomized gas, including oxygen, into chamber 120a to form for example a hyperbaric treatment device or drug treatment device. As noted above, treatment gas, such as oxygen, may be supplied by energy supply system 12, which as noted above may be incorporated into the fluid movement system 30 described above, or by a separate treatment gas bottle 126.

Although in the illustrated embodiment inflatable device 120 is configured to form a mask for a patient's face, it should be appreciated that the inflatable device 120 may be configured to envelope or cover other areas of the patient's body.

Figure 13:
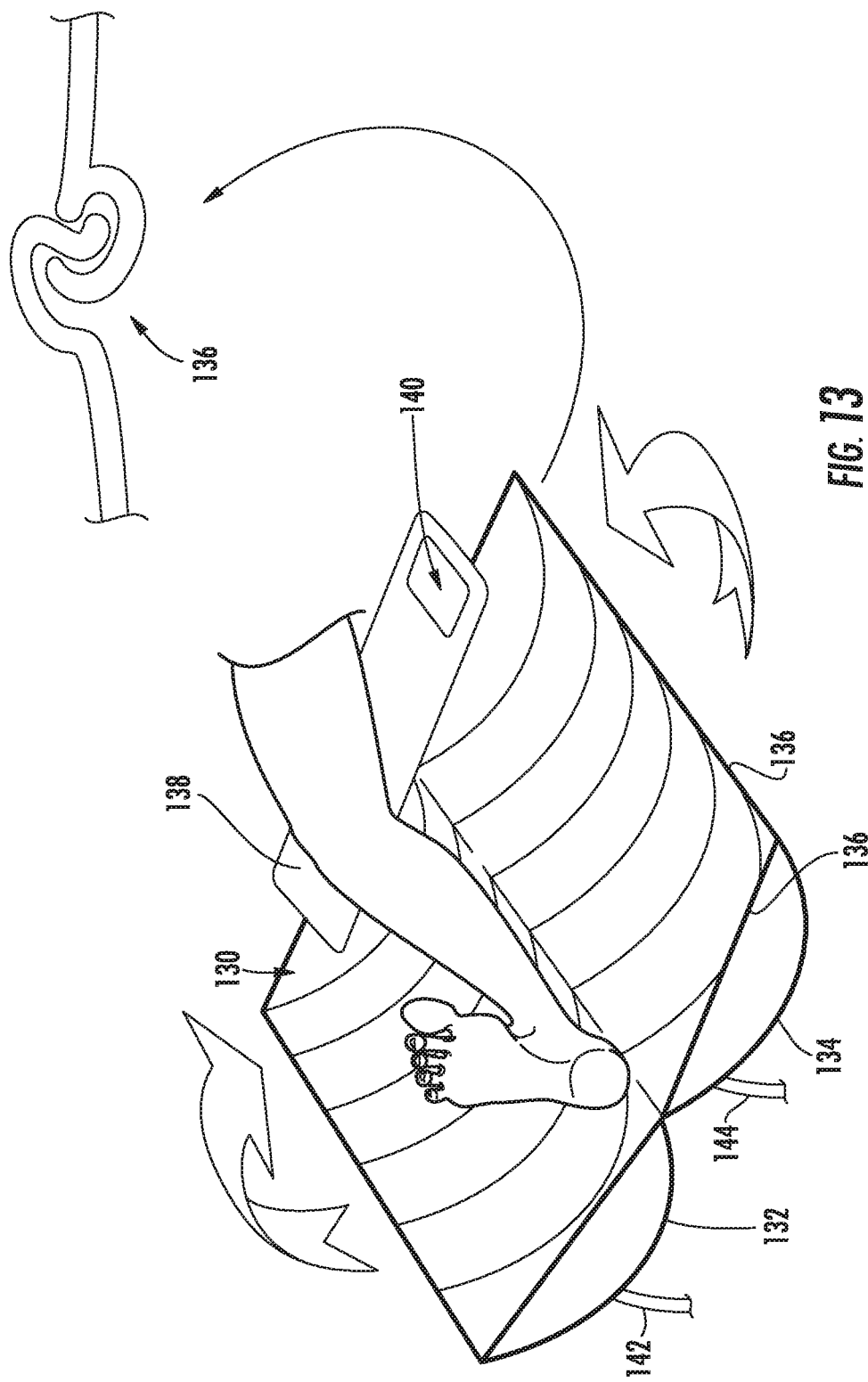
FIG. 13 is a perspective view of another embodiment of a disposable hyperbaric device.

Referring to FIG. 13, the numeral 130 designates another embodiment of an inflatable device. Inflatable device 130 comprises a foldable or wrap-around chamber, which may be positioned around a portion of the patient's body, such as the patient's leg, and used for hyperbaric treatment or vacuum assisted closure treatment or drug treatment, for example. In the illustrated embodiment, inflatable device 130 includes two halves 132 and 134, which fold around, for example, the leg of a patient and is then sealed, for example, by a zip-lock seal 136 along the perimeter portions of the two halves of the chamber. Further, to ensure a proper seal around the appendage of the patient, inflatable device 130 includes a strap or collar 138, which fastens around the patient's appendage, for example using a connector 140, such as an adhesive or a Velcro strip or the like. Alternately, the perimeter portions of the two halves of the device 130 each may include a flange with a sealing surface, which are then clamped together to form an enclosed chamber around the patient's appendage. The folding or wrap-around chamber facilitates the placement of the chamber about the patient's appendage and reduces trauma to the patient when the chamber is deployed around the patient's appendage. Each half 132, 134 of inflatable device 130 may incorporate a conduit, such as a flexible tube for inflating each half of the chamber. Alternately, a single conduit may be used to inflate the entire inflatable device. As will be understood, respective conduits 142 and 144 may be coupled to the ports provided on patient support 10. Further, as noted above, disposable inflatable device 130 may be stored in housing 110, for example (FIG. 11).

Referring to FIGS. 14 and 15, the numeral 150 designates another embodiment of a treatment device that may be incorporated into the present invention. Treatment device 150 may comprise an inflatable device or may comprise a semi-rigid or rigid device that is mounted to a patient support, including patient support 10, for example in an IV support 152 by an articulating arm 154. Arm 154 permits the device 150 to be moved from a deployed position wherein the device 150 is positioned on or at the patient support surface 14 to a stored position in which the device 150 is pivoted by arm 154 behind the footboard 156 of patient support 10. Further, arm 154 may be configured to allow easy removal of device 150 from the patient support for replacement or repair or simply for more permanent storage. In the illustrated embodiment, device 150 forms a treatment chamber, such as a hyperbaric treatment chamber, and includes an opening 158 on one end of the device that allows a portion of the patient's body to be inserted into and extend into the chamber 160 of device 150 and thereby receive treatment in the chamber, for example, a treatment gas, such as oxygen, or vacuum treatment, such as vacuum assisted closure, which is commonly known in the art, or a topical drug treatment. One example of a suitable chamber is disclosed in U.S. Pat. No. 5,060,644, which is incorporated by reference herein in its entirety.

Furthermore, device 150 incorporates a conduit 162 for coupling the chamber to a supply of gas, for example a treatment gas, or to a vacuum pressure. As noted in reference to the previous embodiment, treatment gas or the vacuum pressure may be supplied by energy supply system 12 and, therefore, may similarly be coupled to one of the ports 28a-28d.

Referring to FIGS. 16 and 17, device 150 may alternately be mounted by an arm 164, which permits the chamber to be pivoted between a deployed position on or just slightly above patient support surface 14 to a stored position beneath, for example intermediate frame 22. In the illustrated embodiment, arm 164 comprises generally U-shaped arm with a lower horizontal leg or arm 164a, which extends into a receptacle or socket provided in or below for example intermediate frame 22, and a vertical portion or arm 164b, which supports a second horizontal arm 164c vertically spaced from lower horizontal arm 164a and to which device 150 is mounted. In this manner, when arm 164 is pivoted about lower horizontal arm 164a, device 150 will pivot and move off the patient support surface in an arcuate path to beneath the intermediate frame 22. Similarly, as described in reference to the earlier embodiment, device 150 may be coupled to one of the ports provided on patient support 10 to supply treatment gas (such as oxygen), a vacuum pressure, or a treatment fluid to the chamber of the device.

Further, as best seen in FIG. 17, a second device 150' may be mounted adjacent an opposed side of support surface 14 to provide two devices for patient support 10, which is similarly mounted by an arm 164' that permits device 150' to be moved from a deployed position in which device 150' is either resting or adjacent patient support surface 14 to a stowed position beneath intermediate frame 22. In the illustrated embodiment, devices 150 are configured for providing treatment to a leg of a patient; however, it should be understood that chamber 150 may be configured for treating an arm or another portion of the patient's body.

Referring to FIGS. 18 and 19, another embodiment of a treatment device 250 is illustrated. In the illustrated embodiment, treatment device 250 is a foldable device that can be folded against or into footboard 256 of patient support 10 and then extended to a deployed position, such as shown in FIG. 19. Alternately, treatment device 250 may be configured with an accordion-like side so that treatment device 250 may be fully retracted into the footboard 256 and optionally may be inflated to make the sides rigid, in which case the sides of the device may be inflated by the air supply provided on bed 10.

Referring to FIG. 20, in each of the previous embodiments of the treatment devices, the device may be provided with an energy source 270, such as UV light that provides decontamination of the air in the chamber. In the illustrated embodiment, chamber 350 is of similar construction to chambers 150 and 250. In this manner, in addition to providing a hyperbaric or vacuum assisted closure treatment or drug treatment to a portion of a patient's body, the respective chambers may also provide decontamination and destruction of bacteria that may be located in the chamber or on the patient to facilitate healing.

Figure 22:
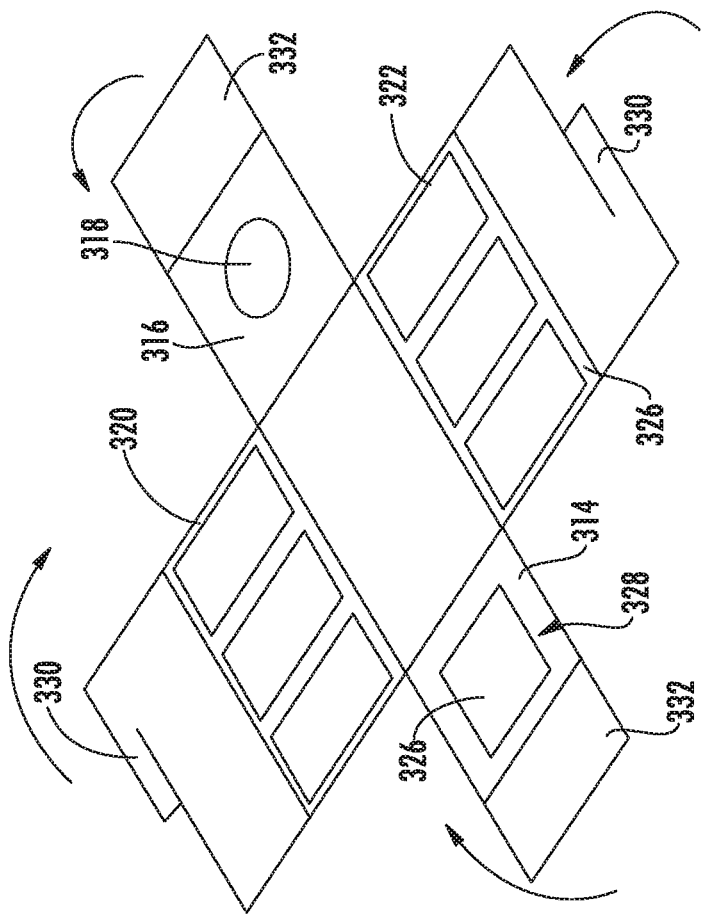
FIG. 22 is a perspective view of the blank that forms the housing.
Figure 21:
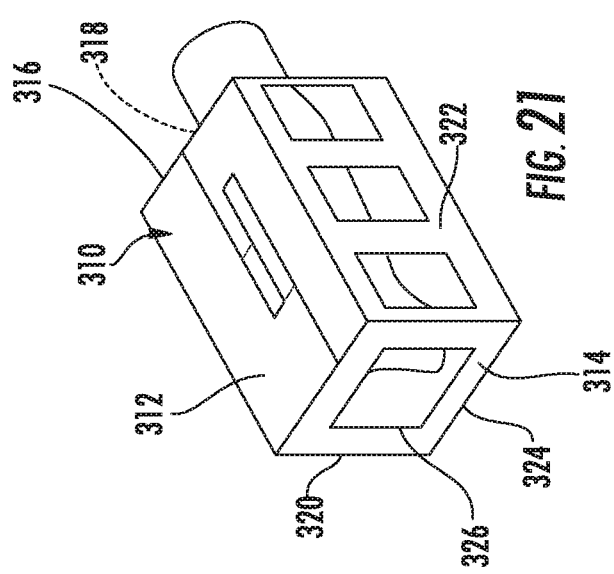
FIG. 21 is a perspective view of a housing that may be used to reinforce an inflatable chamber.

Referring to FIGS. 21 and 22, in the case of the inflatable devices, such as inflatable chambers, the inflatable devices may be optionally provided with a housing 310. Housing 310 provides reinforcement to the respective inflatable device so that when the inflatable device is inflated, the inflatable device may be reinforced and supported by housing 310, which may be particularly suitable for disposable inflatable devices that are preferably formed from plastic sheeting with fairly thin wall thickness.

In the illustrated embodiment, housing 310 includes an upper wall 312 and two opposed end walls 314 and 316, with end wall 316 including an opening 318 to receive an extremity of a patient and the inflatable device, preferably before inflation. Further, housing 310 includes opposed sidewalls 322 and a bottom wall 324. End wall 314 and sidewalls 320 and 322 may include openings 326 formed therein, which provide viewing access to the chamber and the patient's extremity that is treated therein. Referring to FIG. 22, housing 310 may be formed from a blank 328, such as a plastic blank or cardboard blank, which is folded and then secured with interlocking tabs 330 and flaps 332.

Figure 23:
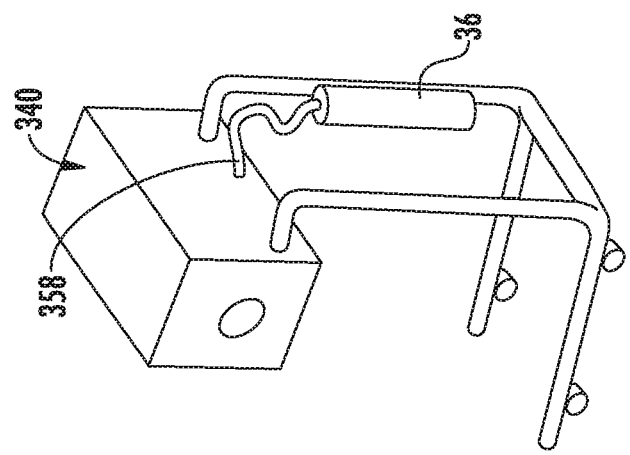
FIG. 23 is a perspective view of a portable chamber that may be used in conjunction with a patient support.
Figure 24:
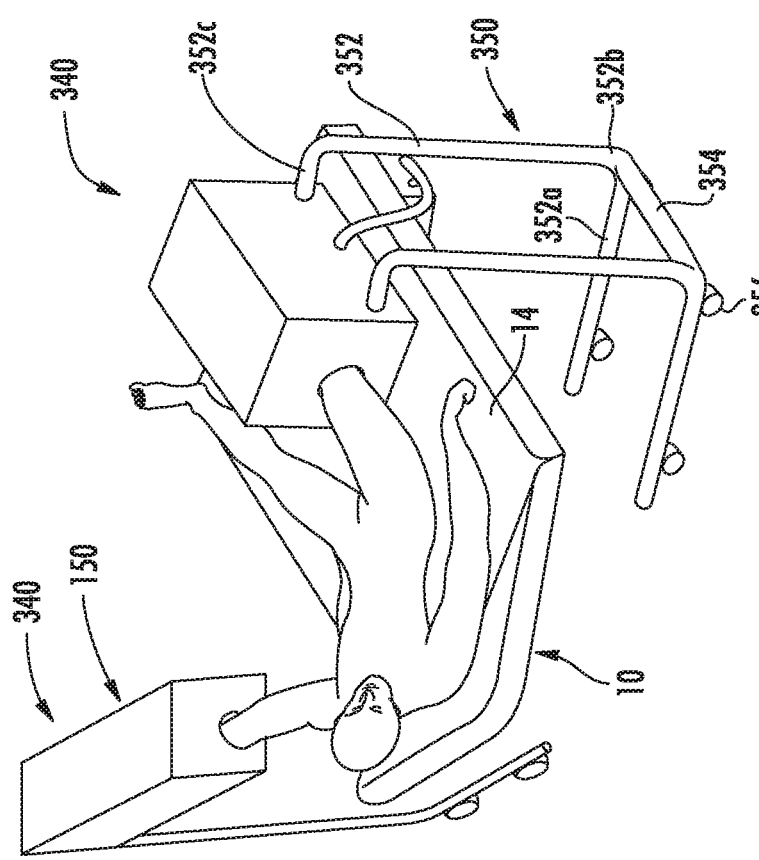
FIG. 24 is a perspective view of a patient support illustrating a patient on the patient support being treated by two of the portable chambers.

Referring to FIGS. 23 and 24, device 150 may be alternately configured as a portable device 340 and mounted to a stand 350, which permits the device to be positioned at multiple positions around the bed, and which therefore provides greater flexibility. Stand 350 is configured so that device 150 is cantilevered from the stand frame 352, which allows the device to be positioned over and optionally on patient support surface 14, similar to the previous embodiments. For example, frame 352 comprises two generally U-shaped side frame members, each with a lower horizontal leg 352a, a vertical leg 352b and a second vertically spaced horizontal leg 352c. The u-shaped side frame members are interconnected by brace or transverse member 354 and further are provided with wheels or rollers 356 to form a wheeled stand to further facilitate movement of the device (150). Device 150 is mounted to arms 352c and as noted above is cantilevered so that device can be positioned over support surface 14.

Treatment gas, such as an atomized gas or drug, or a vacuum pressure is delivered to the chamber of device 150 by a conduit 358. Conduit 358 may be coupled to an external supply, such as an external treatment gas container 360, such as a bottle or an external vacuum source, or may be coupled to the energy supply system through one of the ports 28a-28d, which may act as a conduit to an external fluid or vacuum supply, or an onboard fluid supply or vacuum source.

Figure 27:
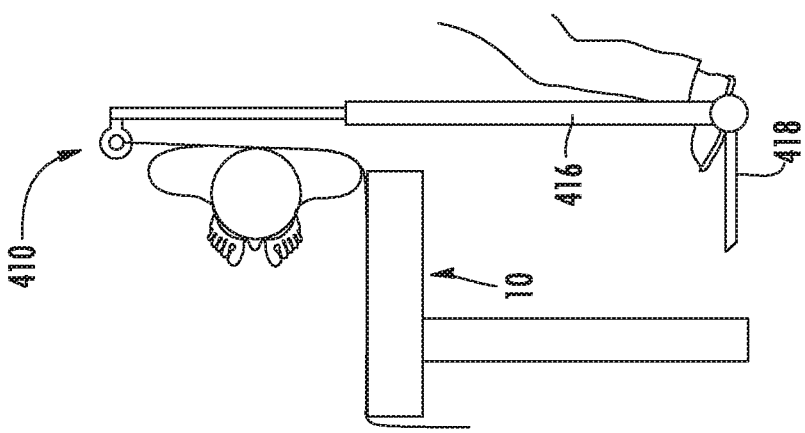
FIG. 27 is a similar view to FIGS. 25 and 26 illustrating the lifting device in the fully extended position.
Figure 26:
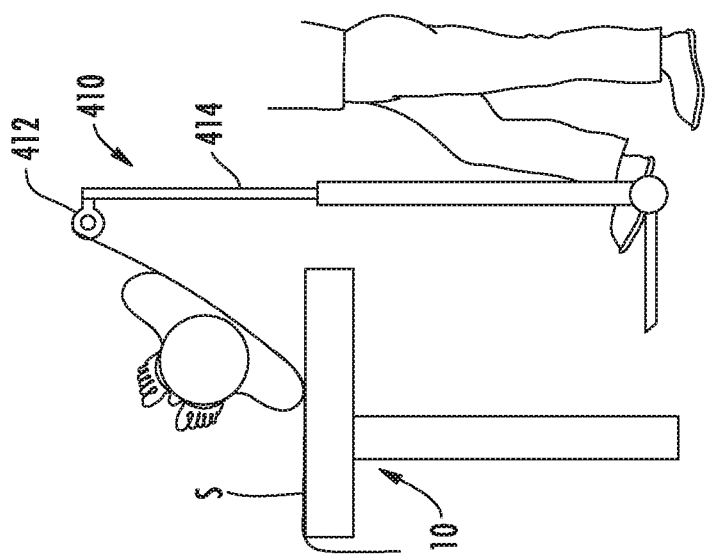
FIG. 26 is a similar view to FIG. 25 illustrating the lifting device in a partially extended position.
Figure 25:
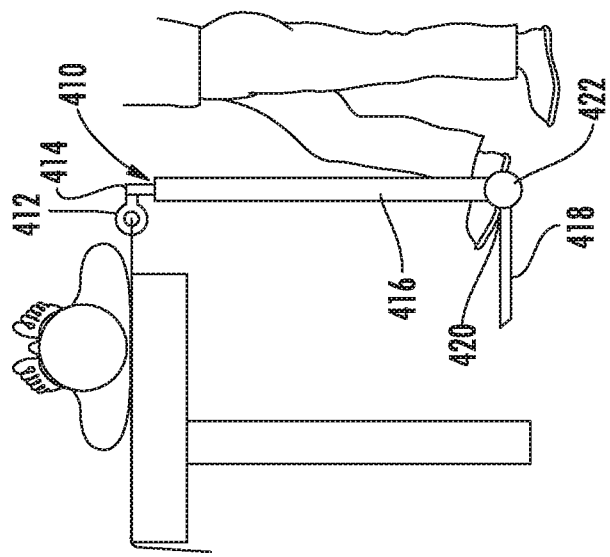
FIG. 25 is a schematic drawing of a lifting device that may be used to assist in turning a patient.

Referring to FIGS. 25-27, the numeral 410 generally designates a lifting device that may be powered by the energy supply system of the present invention. Lift device 410 includes a clamp or retainer 412 for gripping the edge of a sheet S on which a patient is laying. Clamp 412 is mounted at the distal end of an extendible member 414, which is supported for vertical movement relative to a base 418 by member 416. For example, extendible member 414 may be raised relative to base 418 and member 416 by a pneumatic cylinder, which may be powered by energy supply system 12 and housed in member 416. Actuation of the cylinder may be provided by depression of a pedal 420, such as foot pedal, or by a button or switch. Further, lift mechanism 410 may incorporate a wheel or roller 422 to facilitate movement of the lift mechanism.

As best seen in FIGS. 26 and 27, when extendible member 414 extended from member 415, clamp 412 will lift the edge of the sheet, which rolls the patient in a direction away from the lift mechanism.

Referring to FIG. 28, another embodiment of a lifting device 510 that may be powered by the energy supply system of the patient support 10 of the present invention is illustrated. Lifting device 510 includes a housing 512 and a pair of retractable lifting straps or tethers 514 or the like which are raised or lowered by a mechanism contained in housing 512, which may be powered through conduit 516 by energy supply system 12 of patient support 10. Alternately, the lifting mechanism be powered by electricity, which may be provide also by an onboard bed power supply or by an external power supply.

Each strap or tether includes a clamp 514a for gripping the edge of a sheet S on which a patient is laying. Clamps 512 are mounted at the respective distal ends of straps 514, which as noted above are supported for vertical movement relative to support surface 14. For example, straps 514 are wound around a drum and raised relative to surface 14 when the drum is rotated and the straps are coiled around the drum.

Housing 512 is mounted to support 10 by a frame with two vertical arms 510a, 510c and a horizontal arm 510b, which spans between arms 510a and 510c and over the length of the support surface 14. Optionally, housing 512 may be movably mounted to the frame to allow adjustment to the position of housing 512 along the longitudinal axis of support 10, which may be needed when the weight of the patient is concentrated more to one end of the support than the other end.

As would be understood, when straps 514 are retracted into housing 512, the edge of the sheet will be raised causing the patient to roll to one side of the patient support.

Further, the frame may be independently supported from the patient support, for example, on wheels or rollers to facilitate movement of the lift mechanism about support 10 or for transport to another support.

Figure 29:
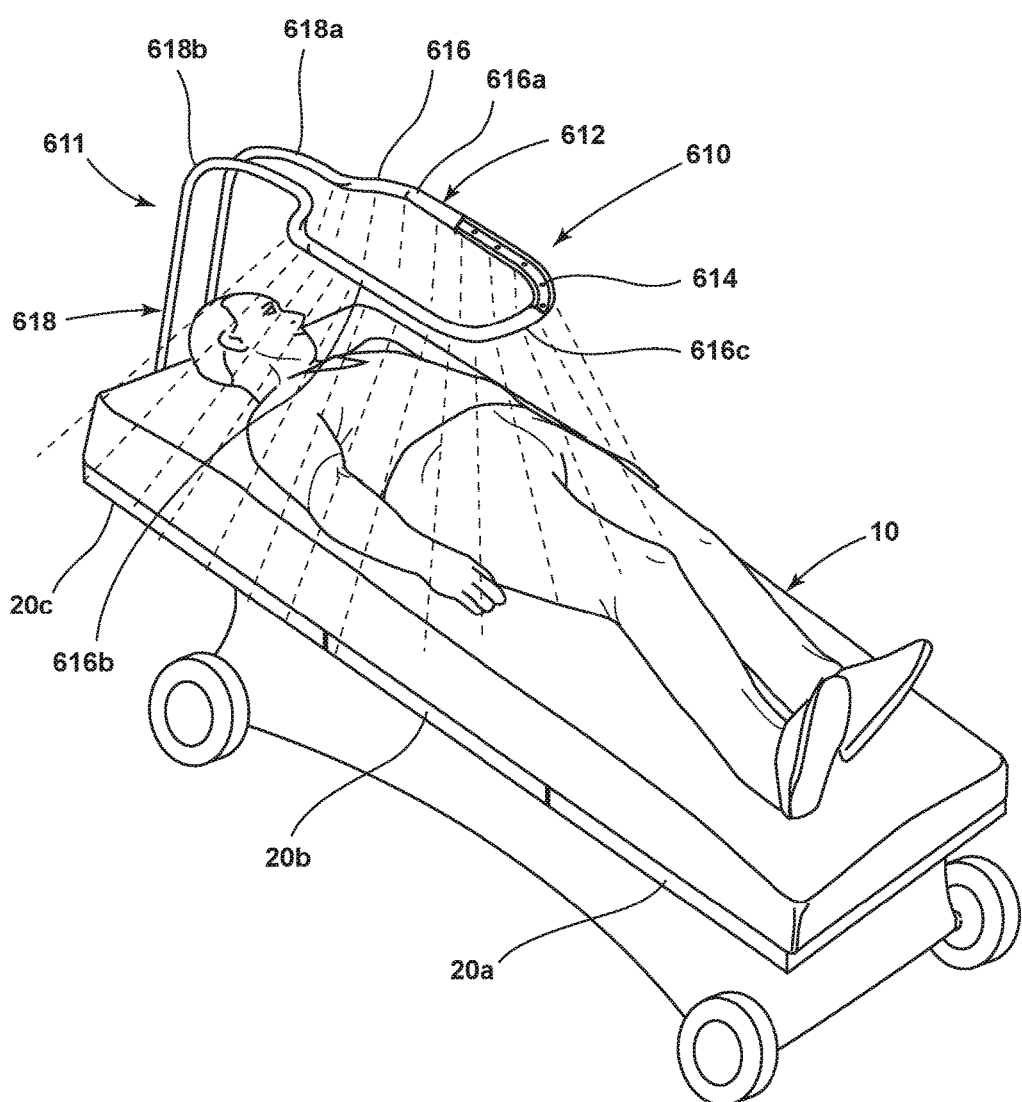
FIG. 29 is a perspective view of a patient support incorporating an airflow apparatus with a frame that directs air flow near or over a patient.

Referring to FIG. 29, the numeral 610 generally designates another embodiment of a device that can be coupled to a port of the fluid movement system of the present invention. Device 610 comprises an airflow apparatus 611 that is configured to direct gas or air over or near a patient with sufficient flow to create a "curtain" that diverts harmful microbes away from the patient so that inadvertent transmission of harmful micro-organisms to a patient can be significantly reduced, if not eliminated, from visitors, family members, other patients in the vicinity, and healthcare professionals or the like.

In the illustrated embodiment, airflow apparatus 611 includes a tubular frame 612, which is formed, for example, from a metal tube, such as stainless steel or aluminum tubing. Further, the tube may be formed from copper, a copper alloy, such as brass, or from a coated metal tubing, for example a metal tube coated with copper or a copper alloy or a silver-based coating to form an antimicrobial surface either inside or outside of the tubing.

To direct air from airflow apparatus 611, frame 612 includes a plurality of openings 614 to direct gas flowing through the frame in the direction of the patient. The openings may be circular or slotted and may be distributed along the full length of the over handing portion 616 of the frame. Gas or air flow is directed into frame 612 either directly from a port described above, for example, by way of a coupler, or frame 612 may be in fluid communication with one or more of the ports by way of a flexible conduit, such as a flex hose or conventional plastic tubing, which includes couplers on both ends, one for coupling to the port and the other for coupling to an inlet of the frame. For example, one or more inlets may be formed in the frame at or near its mount to the bed.

As noted above, frame 612 is formed from a metal tube, which in the illustrated embodiment is configured so that it forms a portion 616 that extends over the patient supported on patient support 10. Portion 616 may have many different configurations but in the illustrated embodiment is formed into a loop, which has two legs 616a and 616b joined at one end by arcuate section 616c, and a mounting base 618 with two arms 618a and 618b. Mounting base 618 is configured to dock into a corresponding pair of sockets provided, for example, at the head end of the patient support 10, and optionally into a pair of sockets provided in the head end of the deck (the fowler) so that the frame moves with the patient when the head end of the bed is raised. The base arms 618a and 618b and/or the sockets (or other mounting structures, such as posts) may include releasable latch mechanisms, such as a spring biased pin and receiving indent or opening, to releasably secure the base 618 to patient support 10. Friction type connections may also be used.

Figure 30:
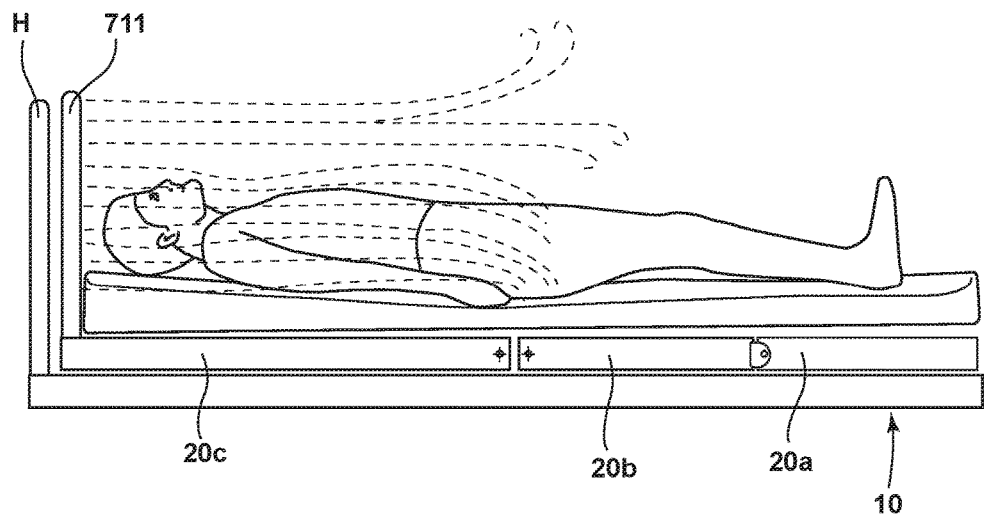
FIG. 30 is a side view of another embodiment of the airflow apparatus.
Figure 31:
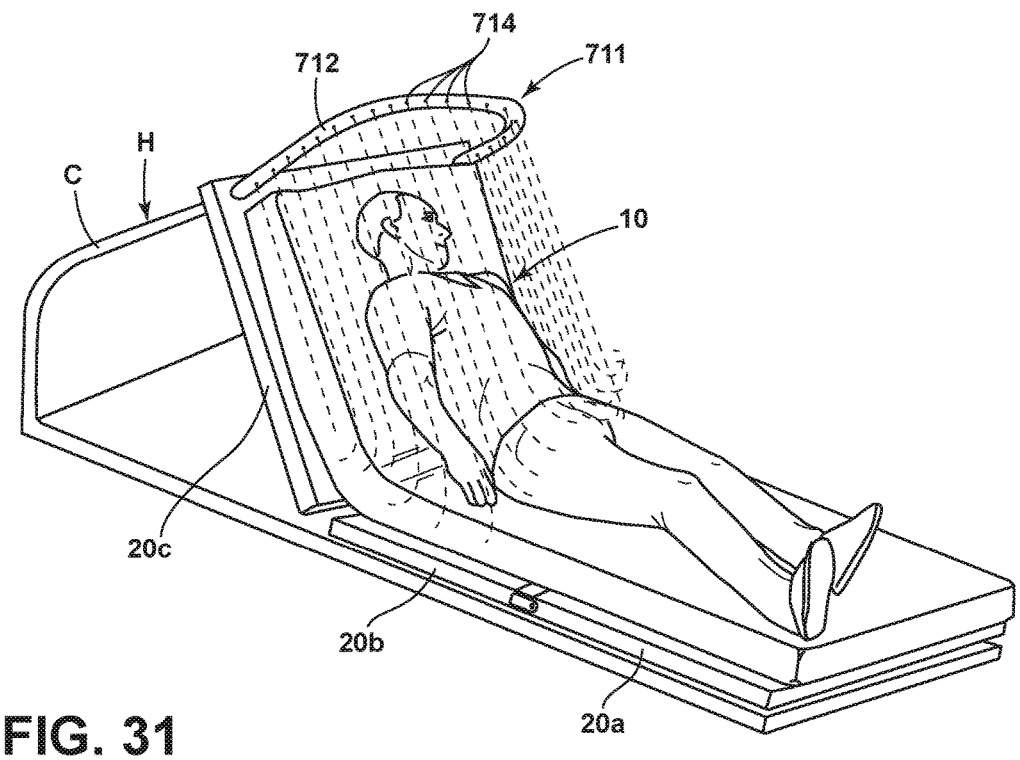
FIG. 31 is a perspective view of the airflow apparatus of FIG. 31.

Alternately, frame 612 may be mounted in or about the headboard of patient support 10. For example, frame 612 may be releasably mounted in or about the headboard so that it can move between a stowed position and a deployed position. Referring to FIGS. 30 and 31, the numeral 711 designates another embodiment of an airflow apparatus. In the illustrated embodiment, apparatus 711 includes a frame 712 with a generally arcuate configuration that optionally follows the contour (C) of the headboard H. Frame 712 is similarly formed from a metal tube, as described above, and includes a plurality of openings to direct the flow of a gas or air across the patient. In this form, the air or gas flow is generally parallel to the patient support surface (e.g. the deck or mattress) of support 10. In this manner, when the patient is lying flat, the frame directs air generally horizontally rather than downwardly as shown in FIG. 29. Similar to the previous embodiment, the ends of frame 712 and corresponding receiving sockets or mounts in or at the deck may include releasable latching mechanisms or friction connections to releasably secure the frame to the patient support.

Figure 32:
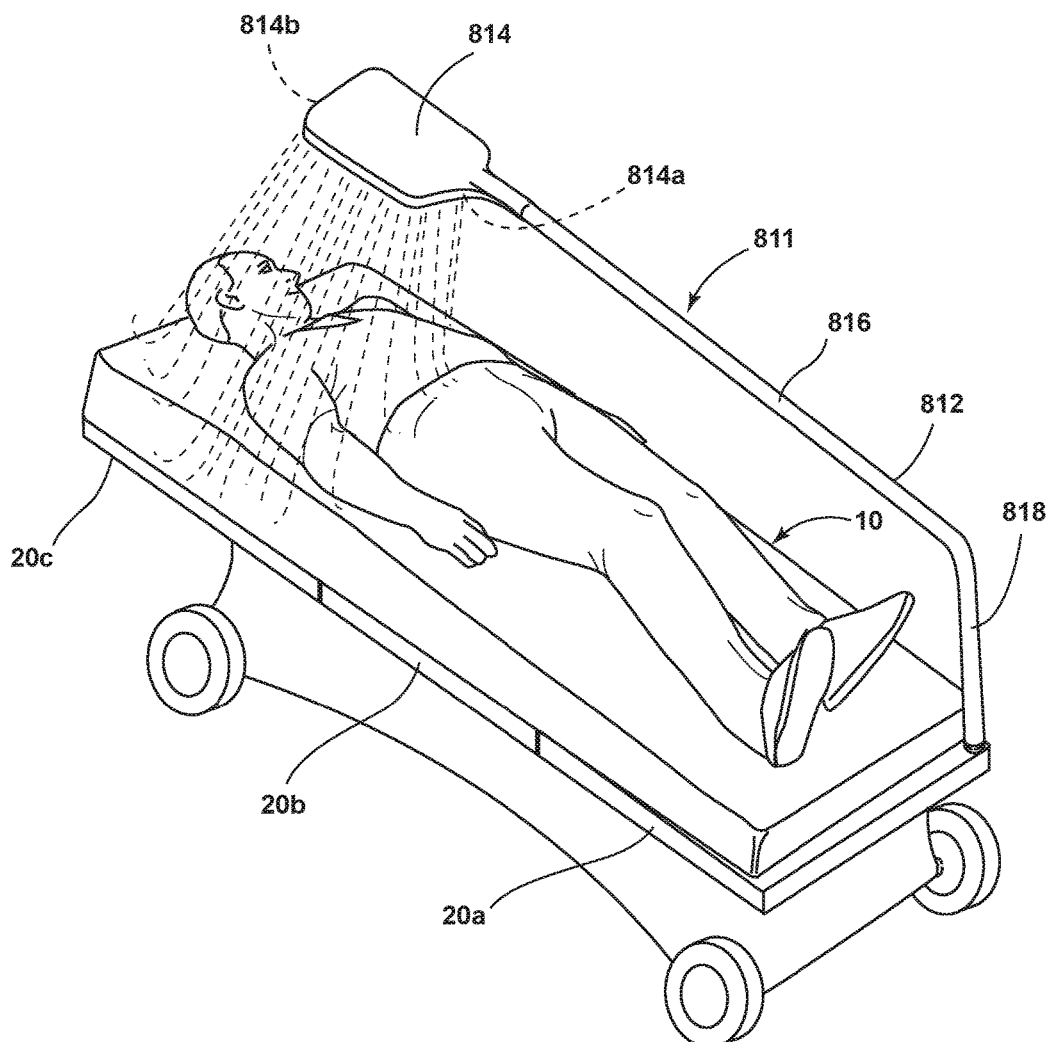
FIG. 32 is a perspective view of a third embodiment of the airflow apparatus.

Referring to FIG. 32, in another embodiment of an airflow apparatus 811, the frame 812 is mounted to the foot end of the patient support. For example, frame 812 may be mounted to the foot end 20a of the deck. Alternately, the frame may be mounted to a side of the patient support 10. In the illustrated embodiment, frame 812 includes an over hanging portion with a generally planar hollowed head 814, which acts as a conduit, and a support arm 816, which extends from mounting base 818. Both support arm 816 and base 818 are formed from tubular members to direct air or gas flow to head 814, which includes a patient facing surface 814a with a plurality of openings 814b to direct air or gas flow downwardly to the patient. The openings may be arranged into a pattern that creates an air curtain that encircles part of the patient's body, such as the head and chest area. It should be understood that the shape of the frame may be varied so that it can create an air or gas curtain that encircles the patient's entire body. Similar to the first embodiment of the airflow apparatus described above, base 818 and corresponding receiving sockets or mounts in or at the support frame or deck may include releasable latching mechanisms or friction connections to releasably secure the base to the patient support.

The air or gas flowing from the frames is optionally filtered to further enhance the infection control function of the flowing air. For example, one or more filters 620 may be included in the fluid movement system described above. Referring to FIG. 8A, filters 620 may be provided in the lines that deliver fluid to the port or ports, which are in fluid communication with the frames.

In addition, the air flowing from the frames may be laminar flow. For example, any of the frames may incorporate a screen or diffuser at or adjacent the openings so that the air or gas that flows from the frames is laminar, which may increase the efficacy of the curtain created by the flow of air. It should therefore be understood that the air flow apparatuses described above direct air or gas flow, including purified, air or gas flow near or over the patient to form a protective gas or air curtain that can protect a patient from harmful airborne microorganisms, which may come from another patient, visitors, or healthcare providers.

Figure 33:
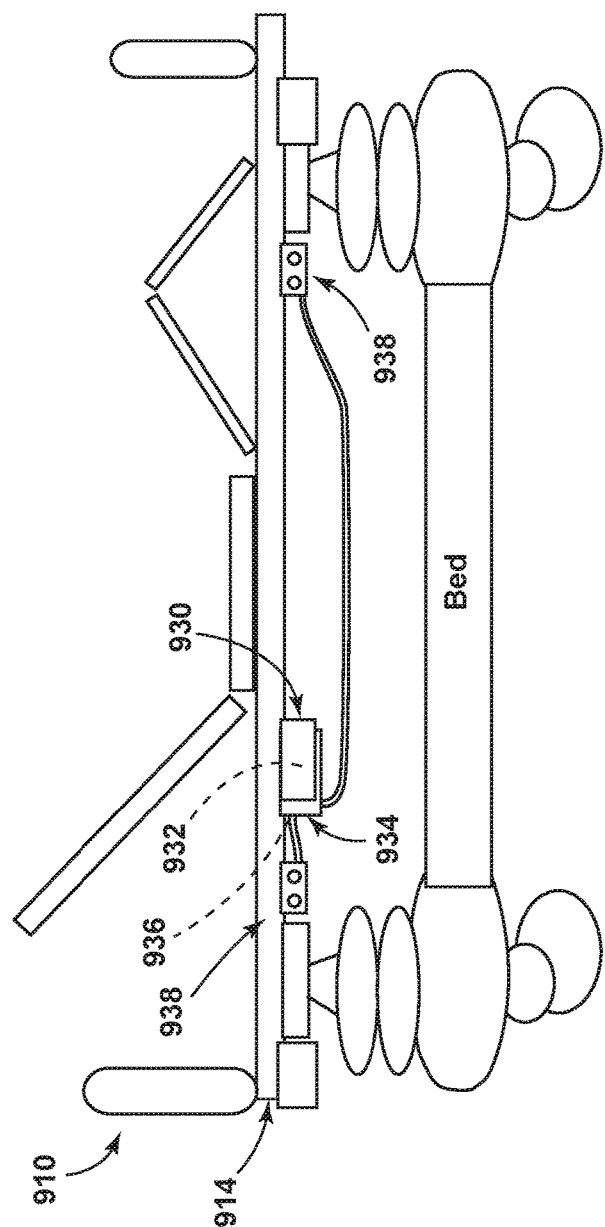
FIG. 33 is a schematic drawing of a patient support incorporating a modular universal energy supply system unit.

Referring to FIG. 33, the fluid movement system may be assembled as a unit 930. Unit 930 may be removable from the patient support 910 for repair, replacement or for transport with a patient. For example, unit 930 may be mounted in a recess 932 formed in patient support 910. In the illustrated embodiment, recess 932 is provided by a bracket 934, which is mounted to support surface 914. As more fully described below, bracket 934 may be configured to provide a one-click coupling of the unit to the patient support and also provide necessary connections between unit 930 and patient support 910 to allow the control system on the patient support to at least communicate with the unit 930.

In the illustrated embodiment, bracket 934 includes a manifold 936, which includes multiple ports for connection via tubing with one or more access ports 938 provided around patient support 910, in a similar fashion to the access ports described above. In the illustrated embodiment, the ports are grouped in pairs at each location, but it should be understood that a single port may be provided at each location. The dual port arrangement allows different devices, which may have different needs, to be coupled to the unit at the same time.

Optionally, bracket 934 may also support electrical contacts for coupling to unit 930 to the power supply on the patient support, for example, to power unit 930 and/or to recharge the power supply in unit 930, more fully described below. In addition, bracket 934 may also support at least one data port for coupling to a corresponding data port on unit 930 to thereby couple unit 930 to the control system on patient support 910.

In this manner, when unit 930 is mounted in patient support 910, unit 930 may provide fluid, such as air, or suction to the access ports, which in turn supply the fluid or suction to the device that is coupled to the access ports, in a similar manner described above. Further, because unit 930 is removable and also may be configured to function independently from patient support 910, unit 930 may be transported with a patient or transferred to a different patient support to provide continuous care for a patient. To that end, unit 930 optionally includes one or more user actuatable devices 930a, such as one or more buttons, switches, or a touch screen, as well as one or more status indicators, such as status indicator lights, including LEDs, for example, on a control panel mounted to the unit to indicate the status and/or state of unit 930.

Figure 34:
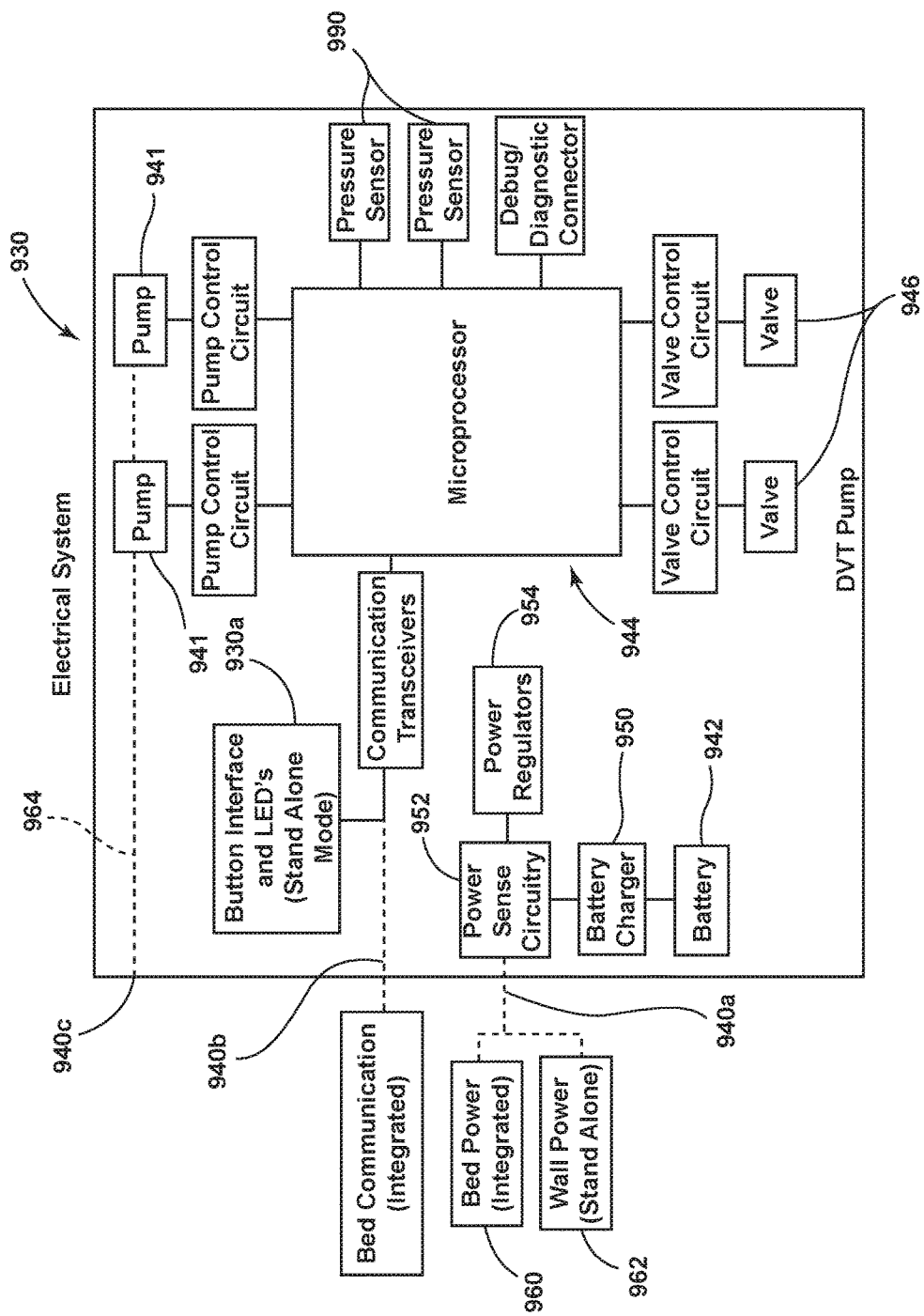
FIG. 34 is a schematic drawing of the modular universal energy supply system unit.

Referring to FIG. 34, unit 930 includes a housing 940 that may be configured to allow one-click installation so that the unit can be mounted into the support single handedly. For example, housing 940 may include multiple connections 940a, 940b, 940c, such as contacts, data ports, and pneumatic ports, aligned on one side of the housing to form a connection interface so that when housing 940 is properly aligned in recess 932 and then inserted into the recess, the connections (940a, 940b, 940c) can align and connect with corresponding connections provided at bracket 934, as noted above. In this manner, housing 940 may include one or more electrical contacts in communication with the patient support based control system and/or at least one pneumatic port in communication with the access ports for directly or indirectly delivering fluid or suctioning fluid to and from a pneumatic device coupled to the access port or ports. Alternately, unit 930 may be positioned such that the unit itself may form the access port or ports.

To protect the connections when unit 930 is being used independently from patient support 910, housing 940 may support a sliding door or cover, including spring biased door, or a pivoting door or cover that is normally in a closed position, but may be opened the user. Alternately or in addition, the door or cover may include a cam surface or structure that cooperates with a corresponding surface or structure on the patient support to open the door when the unit is inserted into the recess.

Figure 34A:
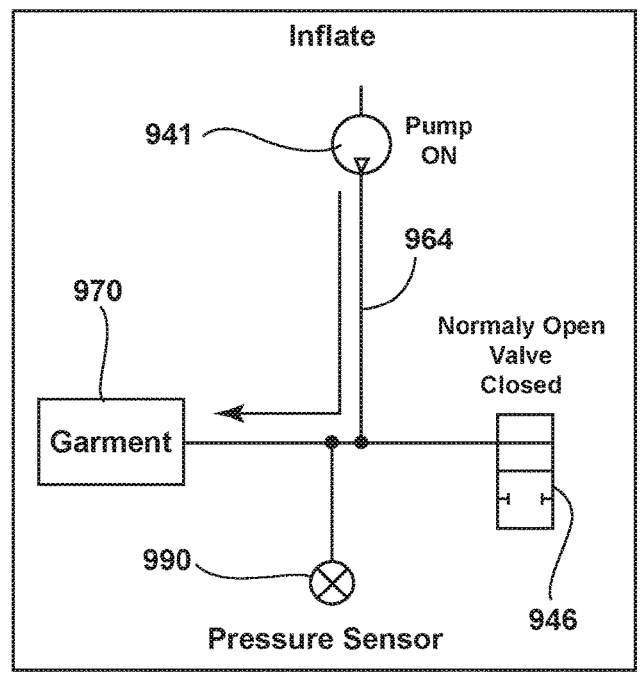
Figure 34B:
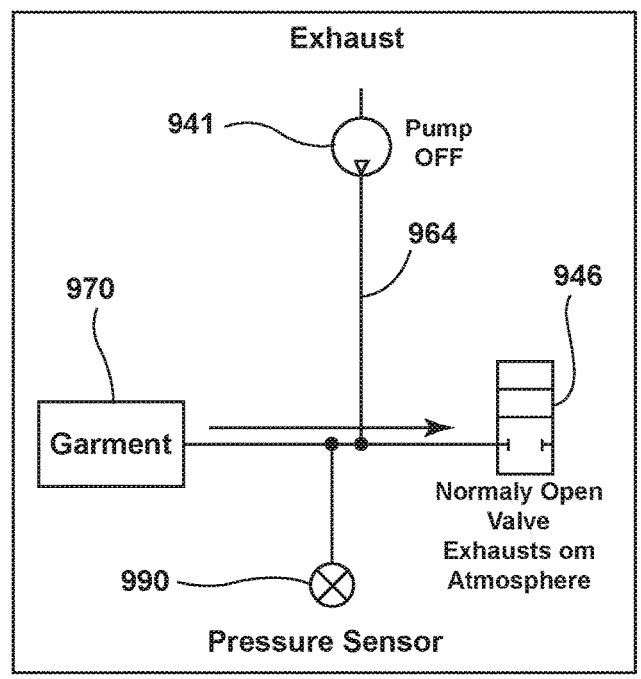
FIG. 34B is a schematic pneumatic drawing of the universal energy supply system unit coupled to a garment when the universal energy supply system unit is off.

Referring to FIG. 34, housing 940 encloses one or more pumps 941, a power supply 942, such as a battery, for powering the pumps, and a microprocessor based control system 944 for controlling the fluid from the pumps. The housing also supports a tubing connection assembly that provides connection ports to connect the unit to tubing to then couple the unit to the access ports or to form the access ports. The pumps are then connected to the tubing connection assembly by tubing 964 (FIGS. 34A, and 34B).

In the illustrated embodiment, the flow of fluid in the tubing is controlled by valves 946. For example, suitable valves include solenoid valves, which are also controlled by control system 944. Further, housing 940 may include a battery charger 950 and power sensing circuit 952, in addition to one or more power regulators 954, which connect the power supply to electrical contacts 940a so that when electrical contacts 940a are coupled to an external power supply, such as a bed-based power supply 960 or wall power supply 962, battery 942 may be recharged. In addition, when the electric contacts 940a are coupled to the external power supply, pumps 941 and microprocessor based control system 944 may be powered directly by the external power supply in lieu of battery 942.

Alternately or in addition, the patient support and unit 930 may each include wireless communication electronics, such as a transceiver (or a receiver and transmitter) to allow the unit to communicate wirelessly with the controller of the patient support when unit 930 is mounted in the patient support or when unit 930 is in close proximity to the patient support. The wireless communication devices may comprise near field wireless communication devices, such as disclosed in U.S. patent application Ser. No. 13/802,992, entitled Communication System for Patient Support Apparatuses filed on Mar. 14, 2013, which is hereby incorporated in its entirety by reference herein. Further, power may be supplied to unit 930 (for recharging or powering) by an inductive power system with inductive coils provided in unit 930 and mounted, for example, near or at recess 932.

In this manner, when the unit is mounted in the patient support, battery 942 may be recharged and/or unit 930 may be powered from the patient support power supply system instead of the unit's battery and further may be controlled by the control system on patient support 910, as described below.

In another embodiment, patient support 910 may include other communication electronics, such as a transceiver (or a receiver and transmitter), to allow the patient support to communicate with another device, which is remote from the patient support, for example a network, including a hospital network, a nurse call station, or a medical records management system. A suitable communication system is disclosed in U.S. patent application Ser. No. 13/802,855, entitled Patient Support Apparatus Communication Systems filed on Mar. 14, 2013 and U.S. patent application Ser. No. 13/570,934, entitled Patient Support Apparatus with In-Room Device Communication filed on Aug. 9, 2012, which are hereby incorporated in their entireties by reference herein. Further, when the unit is in communication with the patient support, the communication electronics of the patient support may be configured to send data or other signals from the unit to the remote device.

In this manner, unit 930 may communicate with the patient support as well as other devices so that the patient support becomes a communication hub for the unit. In addition, unit 930 is operable to send information about itself to the patient support, which can then send the unit's information to the remote device for maintenance, protocol tracking, historic usage etc. For example, unit 930 may generate warnings or alerts, visual or audio, which then may be transmitted by the patient support to the remote device and/or displayed or sounded locally at the patient support, as more fully described below.

Referring to FIGS. 34, 34A and 34B, housing 940 may support pneumatic ports 940c, which are coupled to pumps 941 by way of tubing 964. Valves 946 control the flow of fluid through tubing 964. Referring again to FIGS. 34A and 34B, when the pump or pumps 941 are powered and running, control system 944 actuates valves 946, which are normally open, to close. When closed, valves 946 to allow the flow of fluid from pumps 941 to be directed from tubing 964 to ports 940b and then to the pneumatic device 970, such as a DVT garment, which is coupled to the port(s). To release the pressure in the DVT garment, control system 944 shuts off power to pumps 941 and shuts of power to the valves 946, which causes the valves to open allowing the air accumulated in the garment to flow out of the garment in the discharge through the open valves.

Figure 35:
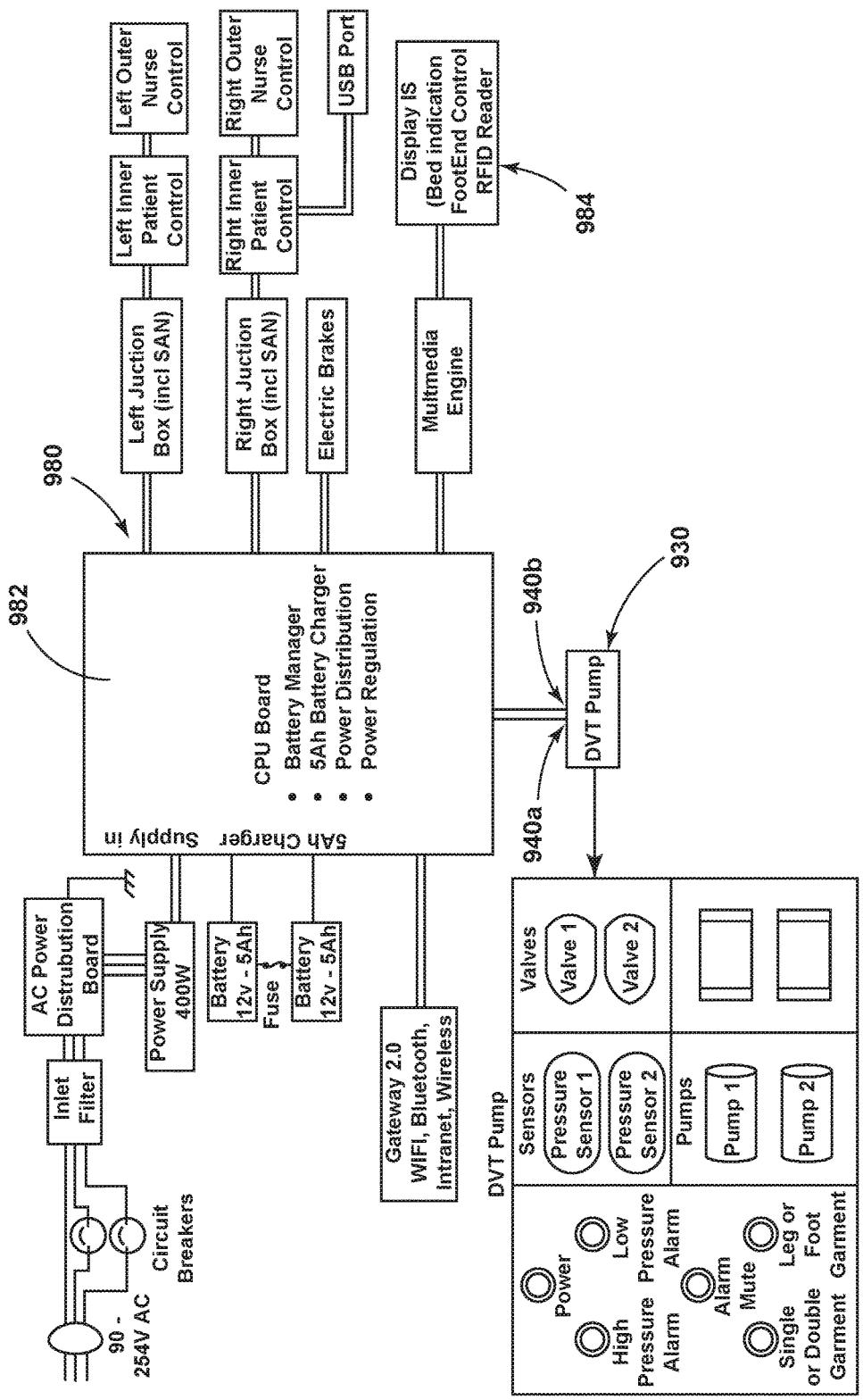
FIG. 35 is a schematic drawing of the modular universal energy supply system unit coupled to the patient support controls and power supply.
Figure 36:
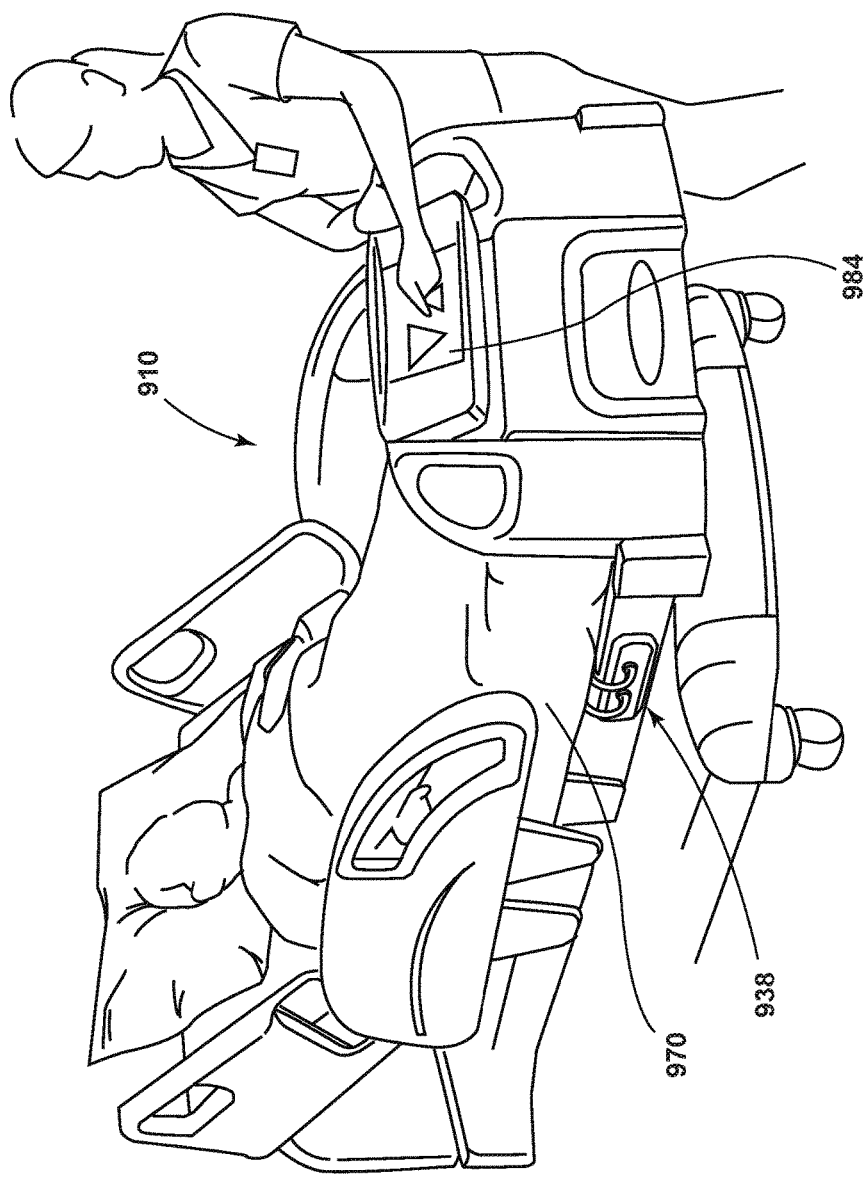
FIG. 36 is a perspective view of the patient support illustrating the display configured for controlling and/or displaying a status of the modular universal energy supply system unit.

Similar to patient support 10, patient support 910 (not shown in FIG. 35) may include a control system 980 with a controller 982 (FIG. 35). As noted above, when unit 930 is mounted in patient support 910, unit 930 may be in communication with controller 982 of patient support 910 via connections 940a and 940b. Alternately or in addition, as noted above, the patient support and unit 930 may each include wireless communication electronics, such as a transceiver (or a receiver and transmitter) to allow the unit to communicate wirelessly with the control system of the patient support when unit 930 is mounted in the patient support or when unit 930 is in close proximity to the patient support.

Optionally, control system 980 includes a user input, such as a display 984, which may be configured to allow control of and/or display the status of unit 930 and/or of the pneumatic device pneumatically coupled to unit 930. For example, referring to FIG. 37, display 984 may comprise a touch screen and, further, display an icon or screen associated with the unit and/or generate a control icon (such as a button or a movable icon) that allows a caregiver to control the operation of unit 930 and the device coupled to the unit. Further, display 984 may include a graphical interface unit (GIU) that forms a menu of options for controlling unit 930 so that a user may customize the operational parameters for unit 930, for example to adjust the rate of pressurization, the hold time, the number of cycles, or to select the type of DVT device.

Further, the control of the unit may be automated, for example, using input from a caregiver during an initial set up or based on parameters about the patient, including patient parameters detected at the patient support as noted below.

As described herein in reference to the embodiments above, control system 980 of the patient support may be able to detect when a pneumatic device is coupled to one of the ports and adjust one or more of the parameters of the fluid movement system to suit the particular device. In addition, as described in U.S. Pat. Nos. 7,690,059 and 8,544,126, which are hereby incorporated in their entireties by reference herein, control system 980 of the patient support may be able to detect when a pneumatic device is coupled to the patient support and generate an icon associate with that device at display and optionally a control icon to control the device.

In another embodiment, unit 930 may be controlled by a virtual control panel, such as described in Ser. No. 14/549,006 (P-446). In addition or alternately, the control of the unit may be automated, for example, using input from a caregiver during an initial set up or based on parameters about the patient, including patient parameters detected at the patient support as noted below.

In order to detect the status of the pneumatic device that is pneumatically controlled by unit 930, unit 930 may include one or more sensors 990 (FIGS. 34, 34A, 34B) in the unit itself (e.g. in each tubing 964) and/or at each connector 940c that connects the pneumatic device to the unit (e.g. at the port). Sensors 990 may comprise pressure sensors, which may be used to control the flow of fluid to the devices, as described below in reference to FIG. 37. Further, unit 930 may have additional sensors, such as other pressure sensors (for detecting high pressure or low pressure), heat sensors, or the like, to detect a fault or alarm condition in the unit and/or connector, which can then be communicated to the patient support controller for either local or remote reporting.

In addition, in one embodiment, patient support 910 may include a monitoring system. The monitoring system may be configured to monitor the status of the unit and further configured to generate reminders to caregivers about the use of the unit. A suitable monitoring and alert system is described in U.S. Pat. Nos. 7,690,059 and 8,544,126, which are hereby incorporated in their entireties by reference herein. For example, when a patient is immobile, the control system may alert a caregiver for the need to use a DVT device on the patient's legs or feet. As noted above, the patient support may have a patient monitoring system, which can be used as input to generate the alert.

Figure 37:
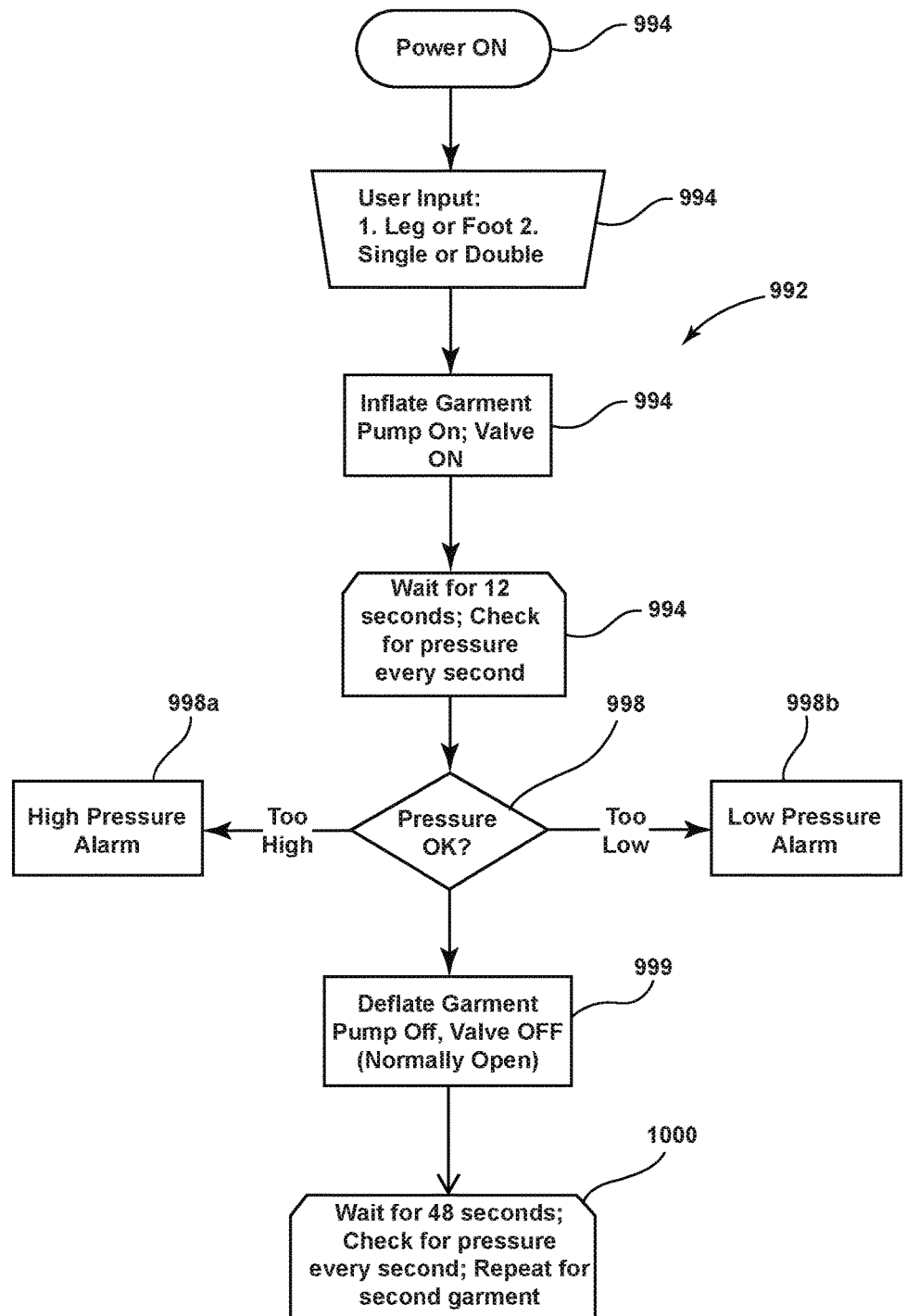
FIG. 37 is a flow diagram illustrating an example DVT inflation and deflation cycle.

When using unit 930 with a DVT device (i.e. a DVT garment, single or double garment, including a leg or foot garment), either the unit-based control system or the patient support based control system initiates a DVT cycle 992, illustrated in FIG. 37, after unit 930 is powered at 994. Unit 930 can be powered on by a user selecting at the display or it may be powered on remotely, for example, by a hand held device or at the nurse call station, for example. The user (locally or remotely) then selects (for example at the display or at the nurse call station) what type of DVT device is to be used 995. After the type of device is selected, the control system powers the pump or pumps to deliver pressurized air to the port to inflate the DVT device 996. For example, for a leg DVT device, the pressure may be in a range of about 30-50 mm of Mercury or about 40 mm of Mercury. For a foot DVT device, the pressure may be in a range of 70-90 mm of Mercury or about 80 mm of Mercury. The control system will then check the pressure by way of the pressure sensor, noted above, for a period of time T1, for example, 10-14 seconds or 12 seconds. The control system will compare the pressure to a low-pressure value and high-pressure value stored in the memory of the control system 998. If the pressure is too high or too low, the control system will generate an alarm signal 998a or 998b. After the period of time has passed, control system will the then shut off (e.g. based on a timing circuit for example or clock at the processor of the control system) and the power to the valves will be shut off, which causes the valves to open, allowing the air in the DVT device to discharge through the valve or valves 999. The process is then repeated after a period of time T2, for example, 46-50 seconds or 48 seconds at 1000 for the same or a second garment. Alternately, the control system may look for a given set of consecutive cycles with a low or high pressure, for example, 5 sets of consecutive cycles, and then terminate the process.

According to yet another embodiment, either the patient support or the pneumatic device may include a sensor to detect if the pneumatic device is being decoupled, for example, when a patient is wearing the pneumatic device and tries to exit the patient support. The sensor may comprise a strain gauge, a pressure sensor for detecting a low pressure, or a displacement sensor, for example. Optionally, the sensor is in communication with either the patient support controller or the unit's controls, which generates an alert signal. For example, the alert signal may be communicated to the patient support from the unit or communicated from the patient support to a remote device, such as a network, a nurse call station, or the like. In this manner the alert signal may be used to prevent damage to the pneumatic device and/or warn when there is potential exit by the patient from patient support.

Alternately patient support 910 may include a patient monitoring system to detect when a patient is about to exit the patient support. A signal or signals from the patient monitoring system may be used by the controller of patient support 910 generate alert signal that the pneumatic device that is being used needs to be decoupled from the port. For example a suitable patient monitoring system includes a bed exit system, such as described in U.S. Pat. No. 5,276,432, or a patient tracking or weight monitoring system, such as described in U.S. Provisional Patent Appl. Ser. No. 61/989,243, entitled Person Support Apparatus with Position Monitoring filed on May 6, 2014, U.S. Provisional Patent Appl. Ser. No. 62/065,242, entitled Methods for Automated and Manual Object Detection and Tracking on a Person Support Apparatus filed on Oct. 17, 2014, and U.S. patent application Ser. No. 14/212,367, entitled Patient Support Apparatus with Patient Information Sensors filed on Mar. 14, 2013, all of which are hereby incorporated in their entireties by reference herein.

Alternately or in addition, the pneumatic device may be coupled to the port using a quick connect coupler, such as a magnetic coupler, including an electromagnetic coupler, or friction-based coupler. Examples of a suitable quick connect couplers are described in U.S. patent application Ser. No. 13/790,762, entitled Patient Support Apparatus Connectors filed on Mar. 8, 2013, which is in and hereby incorporated in its entirety by reference herein. Further, the couplers may be actuated or deactivated based on input from the patient monitoring system. For example, either the controller at the patient support or the control circuit of unit 930 may be coupled to the quick connect coupler and further receive input from the patient monitoring system. Upon receiving a signal that indicates that a patient is trying to exit or appears to be trying to exit the patient support, the patient support controller is configured, for example, to de-energize the magnet so that the pneumatic device can be disconnected without potential damage to the device itself, the coupler, or unit 930.

In another embodiment where the patient support is equipped with an egress button that reconfigures the patient support into a position that allows easier exit from the support, the signal from the egress button may be used as input to the control system to de-energize the magnet or simply to generate an alert signal that the DVT device is still coupled and the patient who is wearing the DVT device appears to want to exit the patient support.

In yet another embodiment, either the unit or the patient support may monitor the usage of the pneumatic device. For example, the pneumatic device may include an RFID tag, which when energized by an RFID tag reader will generate a signal, for example, which can be used either by the patient support controller or the unit's controls to indicate that the device is in use. A counter or timing circuit may be provided, which could keep track of the number of times or the length of time the device has been used. For example, the use may be tracked and compared to a maximum level of use and/or may be tracked for billing purposes. For example of a billing system for software/application usage, reference is made to U.S. patent application Ser. No. 14/211,613, entitled Patient Support Apparatus with Remote Communications filed on Mar. 14, 2014 (STR03B P414B), which is in and hereby incorporated in its entirety by reference herein. Alternately, the DVT device may include an electrical connection to the unit, such as a conductive wire that extends from the unit to a counter on the garment.

Once it is determined that the pneumatic device has been used to its maximum level, then the unit or the patient support may generate an alert signal either locally at the bed, for example, at display 984 or by another indicator, such as a light, for example, an LED. Further, the unit or the patient support may disable the pneumatic device, for example, by disabling its use.

For example, as described above, the patient support control system may be configured to recognize the pneumatic device once it is coupled or in close proximity to the patient support. This may be achieved using a "handshake" or by providing a smart plug-in device in the pneumatic device, which tells the controller what it is. For example, the software in the controller may sign an identification (ID) to the device once the device is coupled near the patient support but then disables use of any device with that identification once it has determined that the device has exceeded its maximum level of use.

For example, the patient support or unit may include a near field communication transceiver that is adapted to communicate with a near field communication transceiver provided on the pneumatic device, for when the device is positioned within a near field vicinity of the near field communication transceiver. The control system or controls (of the unit 930) may then communicate with the near field communication transceiver on the pneumatic device. Optionally, the control system of the patient support is adapted to associate the patient support (or unit) with the pneumatic device when the device is sufficiently near to the patient support or the unit. The association then can be tracked to track the usage of the device, as noted above.

In yet another embodiment, the unit may be controlled based on physiological parameters of a patient or may be controlled so it does not interfere with a treatment being applied at the patient support. For example, the DVT therapy can be controlled or automated, as noted above based on lack of mobility. In addition, for example, if the patient has just had surgery, the treatment may be automated for a given treatment plan following surgery. Further, so as not to interfere with other treatments, the DVT device may be disabled or the treatment terminated, for example, if a blood pressure cuff is being used. For example, the patient support may have an input at the patient support that the caregiver must select when using a blood pressure cuff, which would generate the signal to terminate or disarm the DVT device.

Although primarily described in the context of use with a DVT device, unit 930 may be configured to supply fluid or suction to a variety of different devices. Similarly, in each case the unit may be removed and then be operable independent of the patient support.

Optionally, the patient support may incorporate line management features and/or other types for storage structures for storing the pneumatic devices and/or its accessories, for example, DVT devices (DVT garments), tubing or supplies of tubing and/or other pneumatic devices.

While several forms of the invention have been shown and described, other forms will now be apparent to those skilled in the art. Therefore, it will be understood that the embodiments shown in the drawings and described above are merely for illustrative purposes, and are not intended to limit the scope of the invention which is defined by the claims which follow as interpreted under the principles of patent law including the doctrine of equivalents.

For example, while the energy supply system has been described as providing a vacuum pressure at the ports, it is also contemplated that a separate vacuum system may be coupled to one of the ports via a vacuum generator to reduce contamination of the onboard system. In this manner, the high pressure flow of the fluid from one of the ports may be used generate a vacuum using a venturi effect in the vacuum generator, which is then coupled to a conduit which can then deliver the vacuum pressure where it is desired. These and other modifications may be made, for example, without departing from the scope of the invention as defined by the claims.

We claim:

1. A patient support comprising:
   a patient support surface for supporting a patient thereon, said patient support having a mattress with at least one inflatable bladder and a pneumatic system, said pneumatic system being in fluid communication with the inflatable bladder and including a plurality of ports mounted to said patient support, each of said ports being accessible by a user for coupling an external device to said pneumatic system;
   a DVT assembly having a housing and a DVT pump mounted in said housing, said DVT assembly being configured to mount to said patient support relative to said patient support surface, and when mounted to said patient support said DVT pump configured to be in fluid communication with said pneumatic system of said patient support
   for delivering fluid to at least one port of said ports, and said at least one said port configured for coupling to a DVT device for delivering fluid to the DVT device from said DVT pump when the DVT pump is in fluid communication with said pneumatic system of said patient support and after a user has coupled the DVT device to said at least one port; and
   a patient support control system mounted in said patient support to control one more of components of said patient support and configured to communicate with the DVT assembly, and said control system configured to send signals to the DVT assembly to control the DVT pump.

2. The patient support according to claim 1, wherein said control system is configured to receive signals from said DVT assembly and includes a communication device for communicating with a remote device, and said control system configured to send signals relative to the DVT assembly to the remote device wherein said patient support becomes a communication hub for the DVT assembly.

3. The patient support according to claim 2, said control system including a wireless communication device for wireless communication with the remote device.

4. The patient support according to claim 2, wherein each of said control system and said DVT assembly includes a wireless communication device for wireless communication between said control system and said DVT assembly.

5. The patient support according to claim 4, wherein said wireless communication devices comprise near field wireless communication devices.

6. The patient support according to claim 4, further in combination with a DVT device, wherein said DVT device generates data signals containing data about said DVT device, said DVT device being operable to transmit said data signals to said communication device of said control system of said patient support, and said communication device of said control system configured to transmit said data signals to the remote device for maintenance of said DVT device, protocol tracking of said DVT device, and/or historic usage information of said DVT device.

7. The patient support according to claim 1, said patient support control system further comprising a user input, said user input configured to allow control of and/or display of a status of the DVT device.

8. The patient support according to claim 1, further comprising a monitoring system, said monitoring system configured to monitor a status of the DVT device and further configured to generate a reminder to a caregiver about use of the DVT device.

9. The patient support according to claim 8, said DVT assembly further comprising a user interface, said user interface configured to allow a caregiver to monitor and/or select a protocol for the DVT device.

10. The patient support according to claim 9, wherein said user interface is in wireless communication with said control system of said patient support to allow control of and/or monitoring of the DVT device through said patient support control system of said patient support.

11. The patient support according to claim 1, wherein said patient support control system includes a user interface configured to allow a caregiver to set a reminder for a protocol for the DVT device.

12. A patient support comprising:
   an inflatable bladder forming a patient support surface to support a patient;
   a patient support based control system mounted in said patient support and for controlling one or more components of said patient support;
   a patient support based pneumatic system in fluid communication with said inflatable bladder for inflating or deflating said inflatable bladder;
   a recess provided in said patient support, said recess having a connection coupled to said control system and a first port in fluid communication with said patient support based pneumatic system;
   a DVT housing having a DVT pump, said DVT housing being configured to mount relative to said patient support surface, said DVT housing configured to couple to said connection and said first port of said recess when said DVT housing is mounted in said recess to couple said DVT pump to said control system and to said patient support based pneumatic system;
   said patient support further having a second port accessible by a user, and said second port in fluid communication with said DVT pump via said patient support based pneumatic system when said DVT housing is mounted in said recess and said DVT pump is in fluid communication with said pneumatic system;
   a DVT device, said second port configured to couple to said DVT device to deliver fluid to said DVT device from said DVT pump after said DVT device is coupled to said second port; and
   said DVT device including a communication device configured to send data and/or other signals to said control system on said patient support.

13. The patient support according to claim 12, wherein said DVT device generates data signals containing data about said DVT device, said communication device of said DVT device being operable to send said data signals to said control system for maintenance of said DVT device, protocol tracking of said DVT device, and/or historic usage information of said DVT device.

14. The patient support according to claim 12, wherein said DVT device is configured to generate warnings or alerts.

15. The patient support according to claim 14, wherein said control system is operable to transmit said warnings or alerts to a remote device.

16. The patient support according to claim 14, wherein said control system is operable to display or sound said warnings or alerts locally at said patient support.

17. The patient support according to claim 14 further comprising a display operable to display said warnings or alerts.

18. The patient support according to claim 12, further comprising one or more sensors to detect a fault or alarm condition at said DVT device.

19. The patient support according to claim 12, wherein said control system is configured to detect when said DVT device is coupled to or in close proximity to said patient support.

20. The patient support according to claim 12, wherein said patient support comprises a bed.

* * * * *